(12) United States Patent
Mousa et al.

(10) Patent No.: US 7,741,311 B2
(45) Date of Patent: Jun. 22, 2010

(54) COMPOSITION AND METHOD FOR TREATING OCCLUSIVE VASCULAR DISEASES, NERVE REGENERATION, AND WOUND HEALING

(76) Inventors: Shaker Mousa, 5 Fox Glove Ct., Wynantskill, NY (US) 12198; Robert Linhardt, 214 Lancaster St., Albany, NY (US) 12210

( * ) Notice: Subject to any disclaimer, the term of this patent is extended or adjusted under 35 U.S.C. 154(b) by 802 days.

(21) Appl. No.: 11/324,702

(22) Filed: Jan. 3, 2006

(65) Prior Publication Data

US 2006/0147415 A1 Jul. 6, 2006

Related U.S. Application Data

(60) Provisional application No. 60/641,293, filed on Jan. 3, 2005.

(51) Int. Cl.
*A61K 31/70* (2006.01)
*C07H 15/00* (2006.01)

(52) U.S. Cl. .................. 514/54; 536/4; 536/1; 536/55.2
(58) Field of Classification Search .................. None
See application file for complete search history.

(56) References Cited

U.S. PATENT DOCUMENTS 5,977,080 A * 11/1999 Rosen et al. .................. 514/25
2003/0176395 A1* 9/2003 Sakai et al. .................. 514/54

\* cited by examiner

*Primary Examiner*—Elli Peselev
(74) *Attorney, Agent, or Firm*—Schmeiser, Olsen & Watts, LLP

(57) ABSTRACT

A composition and a method of treating a subject with respect to a pathological condition comprised by the subject. The composition comprises a sulfated saccharide conjugated to a polymer. The method comprises administering to the subject a composition comprising a sulfated saccharide conjugated to a polymer or a sulfated saccharide. The sulfated saccharide has a molecular weight less than 5000 Dalton.

57 Claims, 27 Drawing Sheets

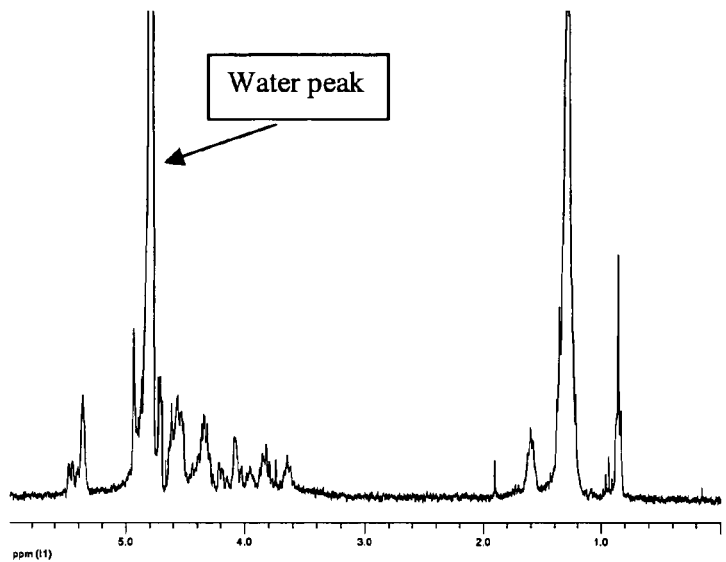
FIG. 1    NMR for Sulfated Fucose Tetrasaccharide 12
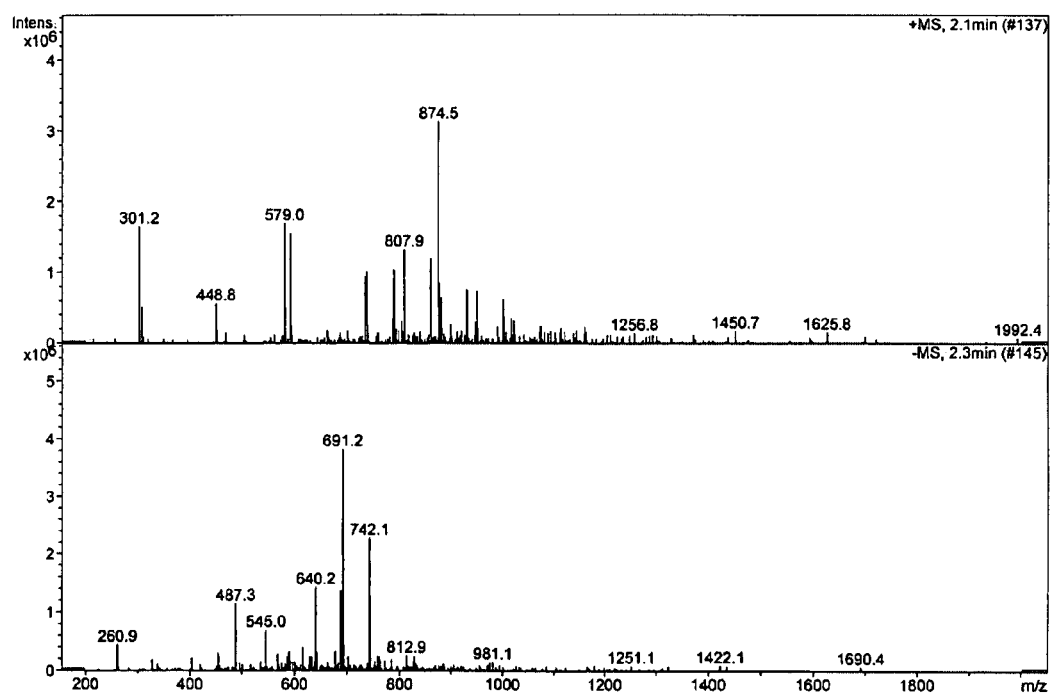
FIG. 2    MS for Sulfated Fucose Tetrasaccharide 12

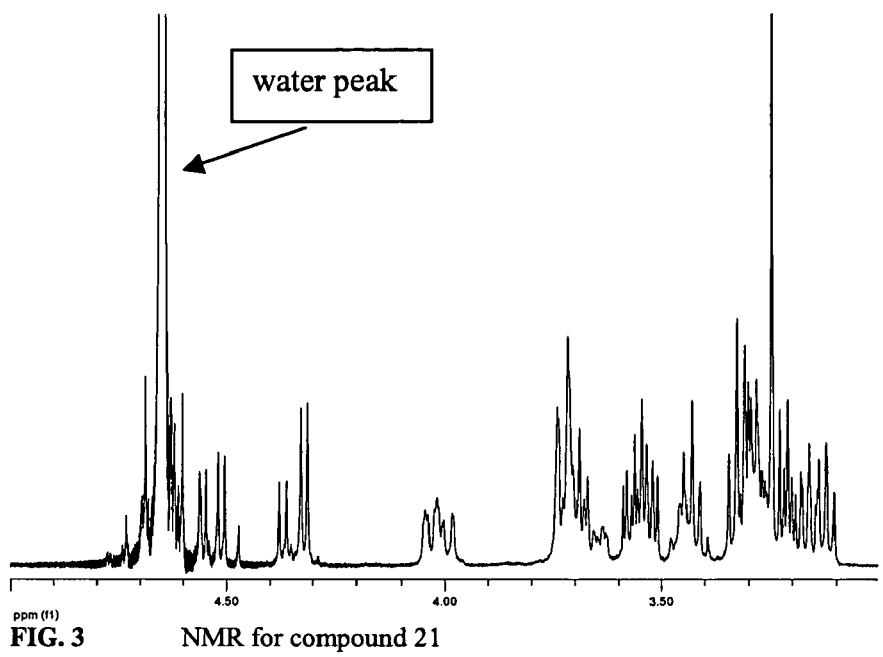
FIG. 3  NMR for compound 21
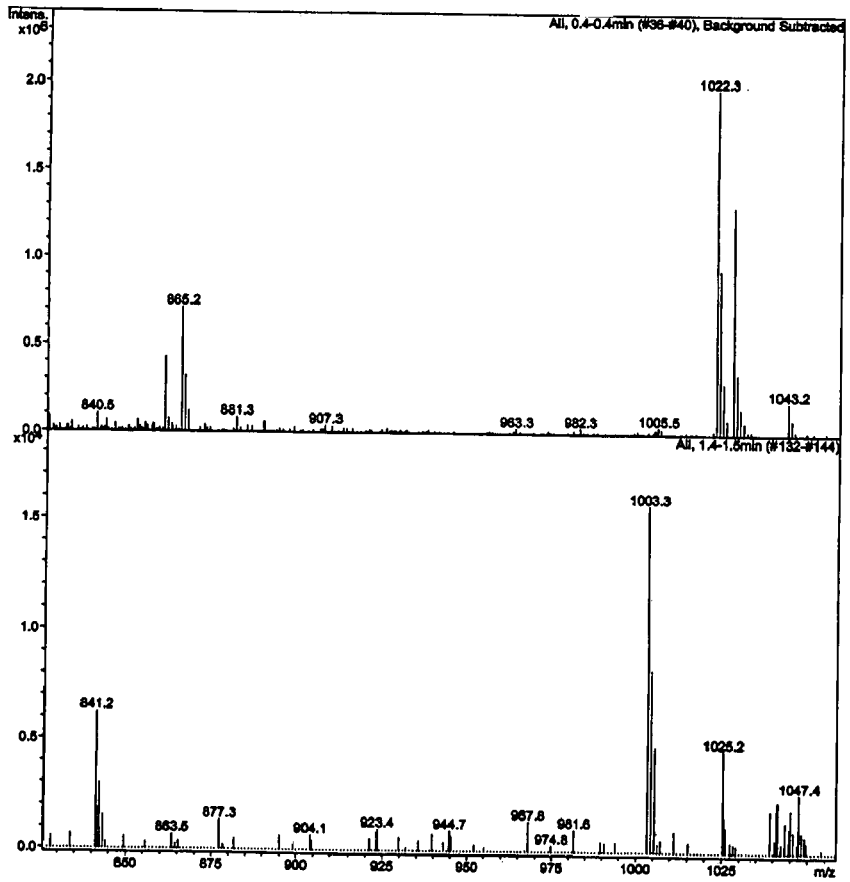
FIG. 4  MS for compound 21

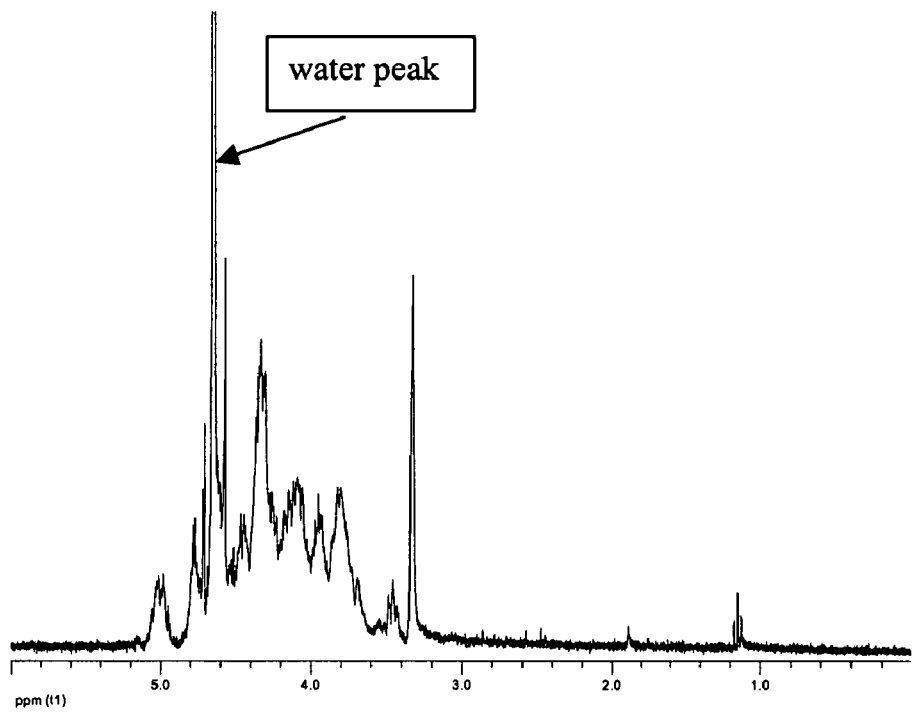
FIG. 5 NMR for Sulfated Hexa-β-D-glucopyranoside 22
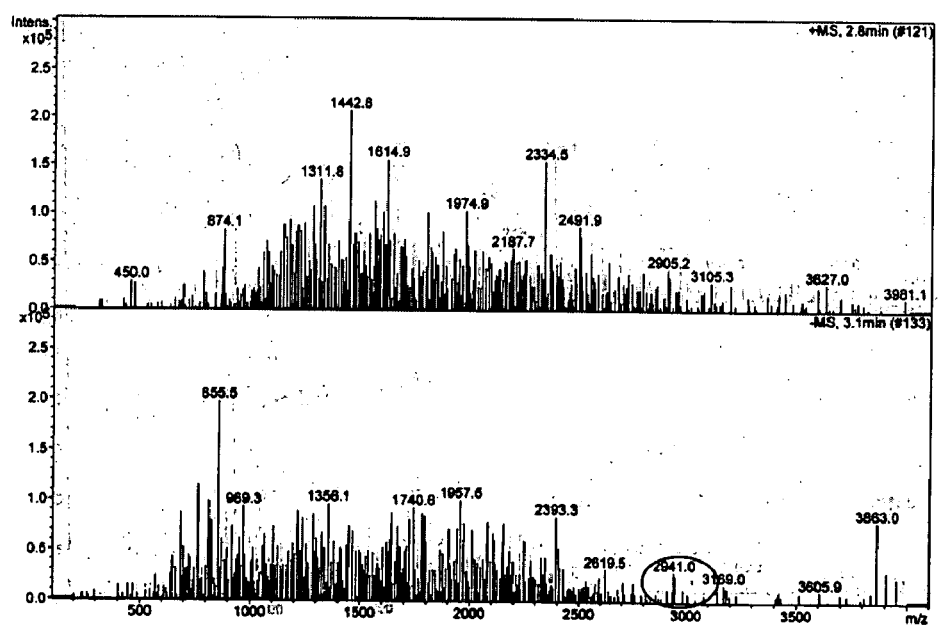
FIG. 6 MS for Sulfated Hexa-β-D-glucopyranoside 22

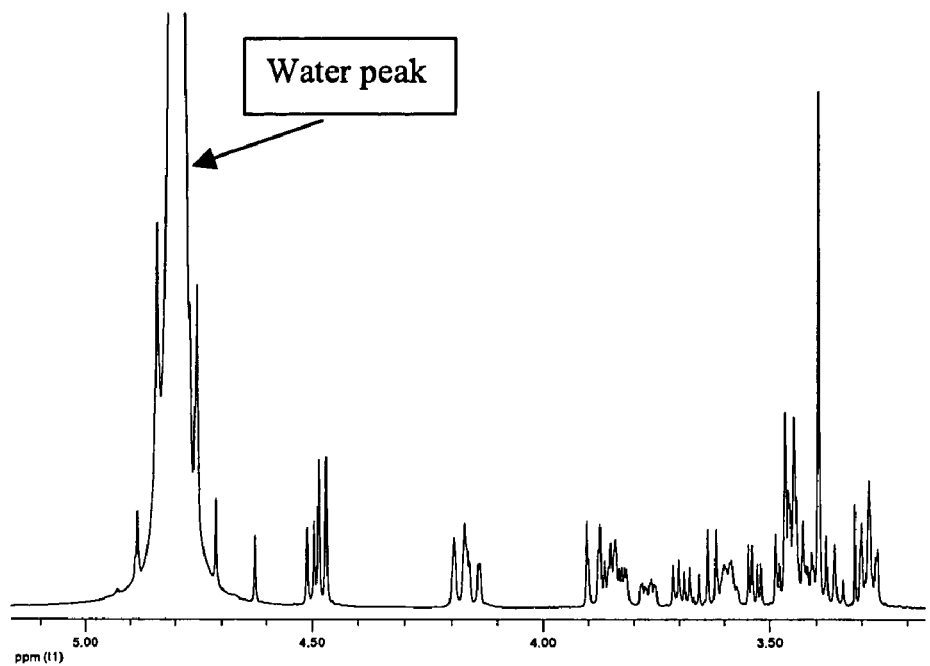
FIG. 7  NMR for compound 36a
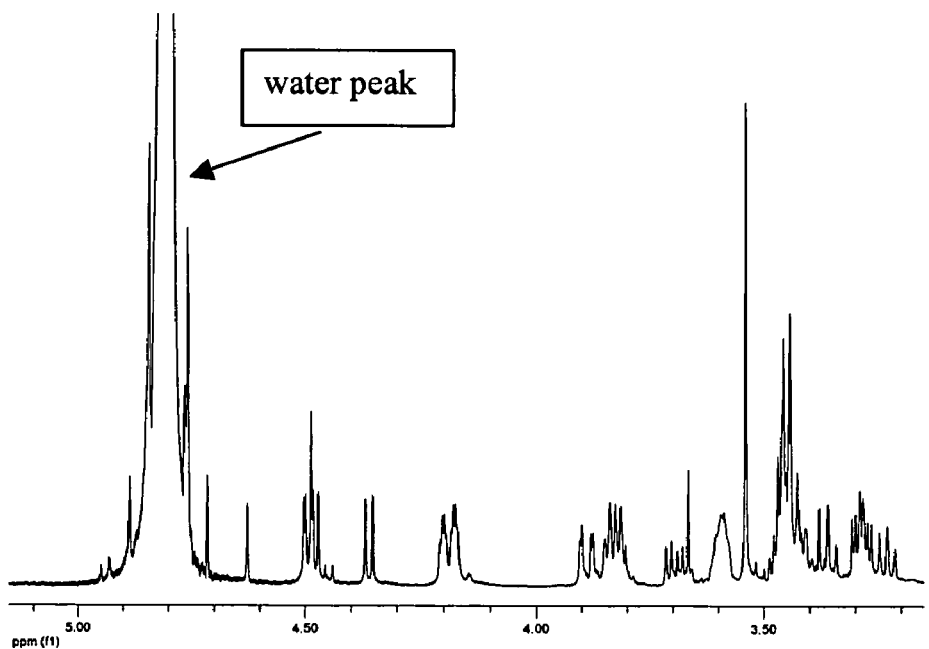
FIG. 8  NMR for compound 36b

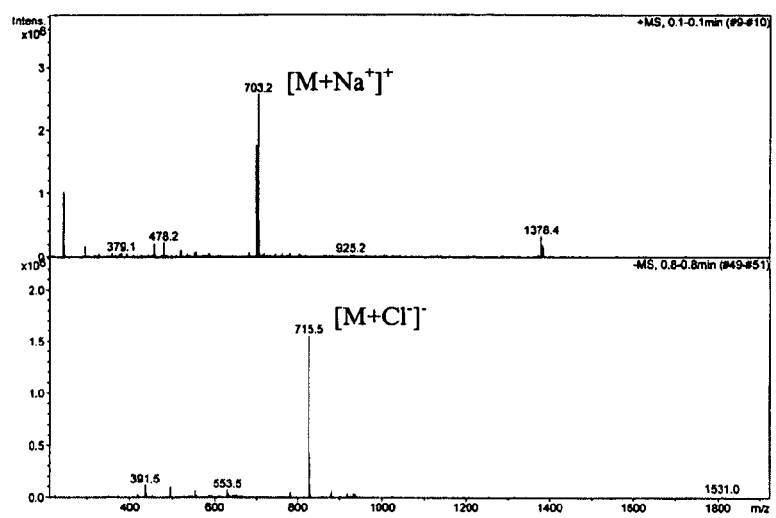
FIG. 9   MS for compound 36a
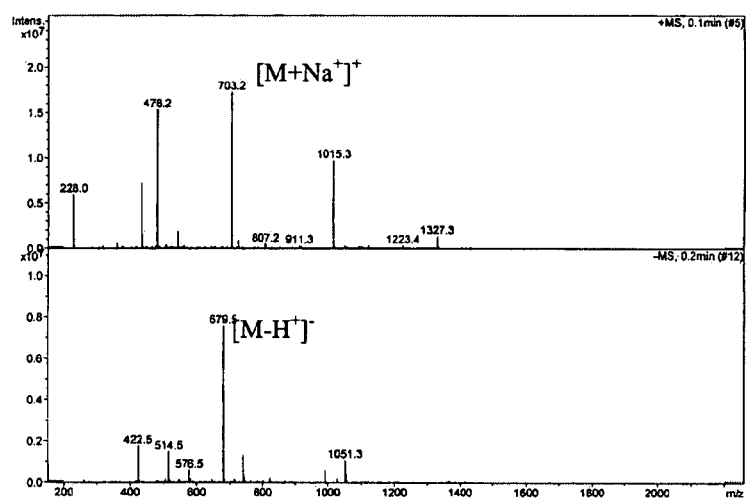
FIG. 10   MS for compound 36b
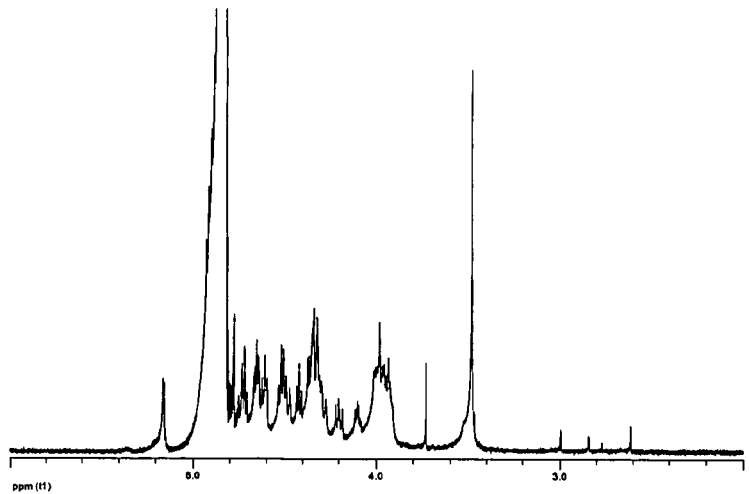
FIG. 11   NMR for compound 37a

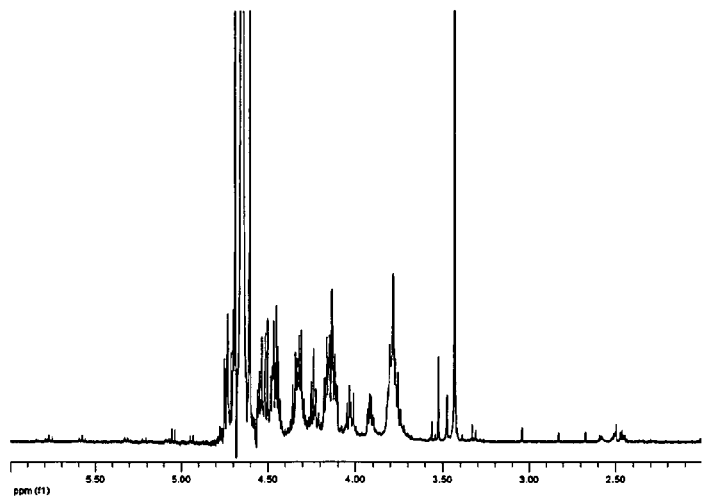
FIG. 12  NMR for compound 37b
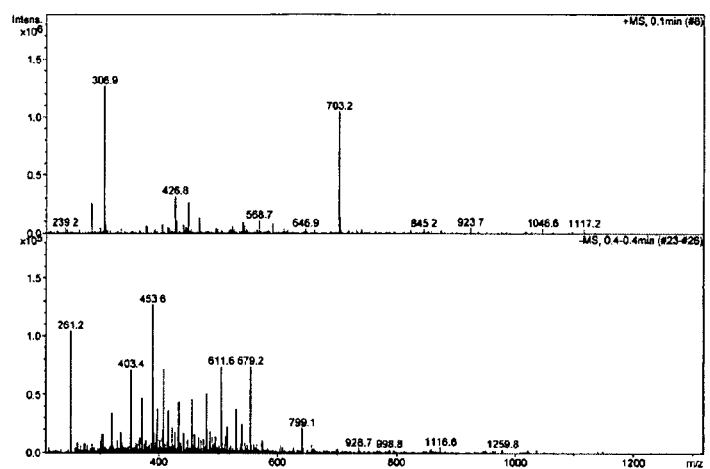
FIG. 13  MS for compound 37a
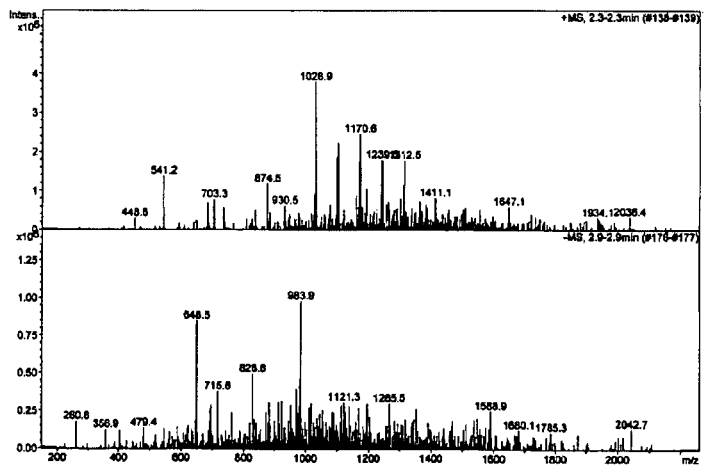
FIG. 14: MS for compound 37b

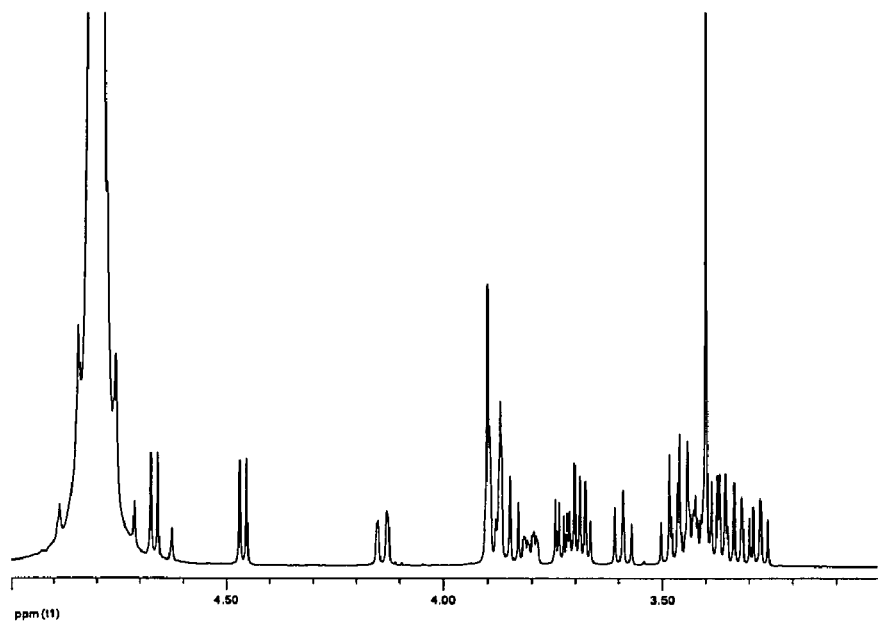
FIG. 15   NMR for compound 43
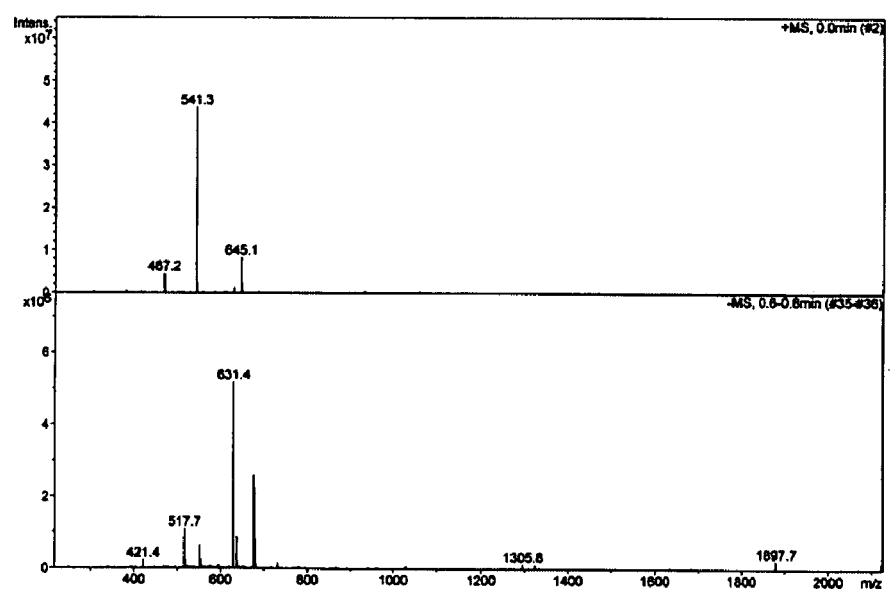
FIG. 16   MS for compound 43

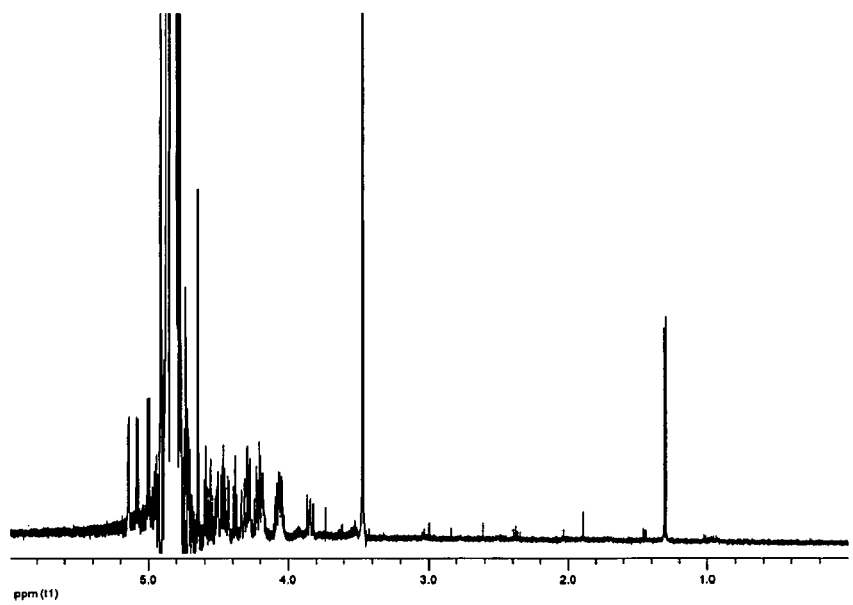
FIG. 17  NMR for Tri-β-D-glucopyranoside 44.
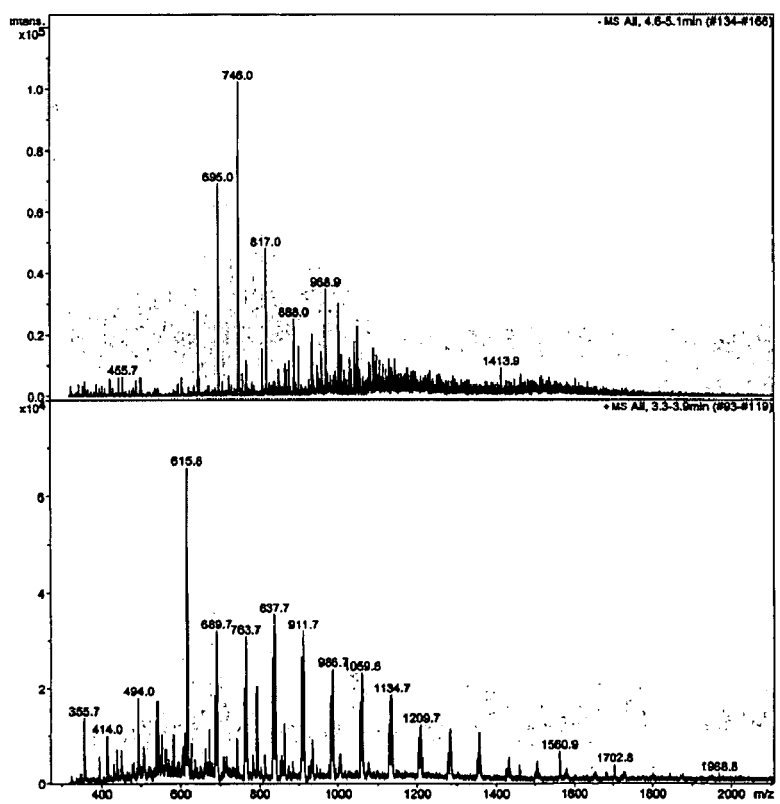
FIG. 18  MS for Tri-β-D-glucopyranoside 44.

In vitro 3-D Human Angiogenesis Assay
Step I: culture of HDMEC on microcarrier beads (EC-beads)
Step II: culture of EC-beads in 3-D ECM gel +/- angiog factor
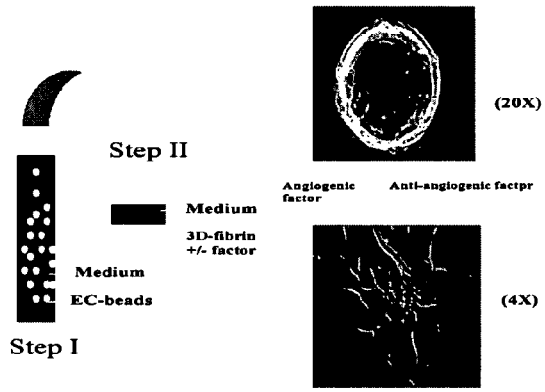
FIG. 19 In vitro 3-D Sprout angiogenesis model
Stimulation of Angiogenesis by Sulfated Saccharides in the CAM Model
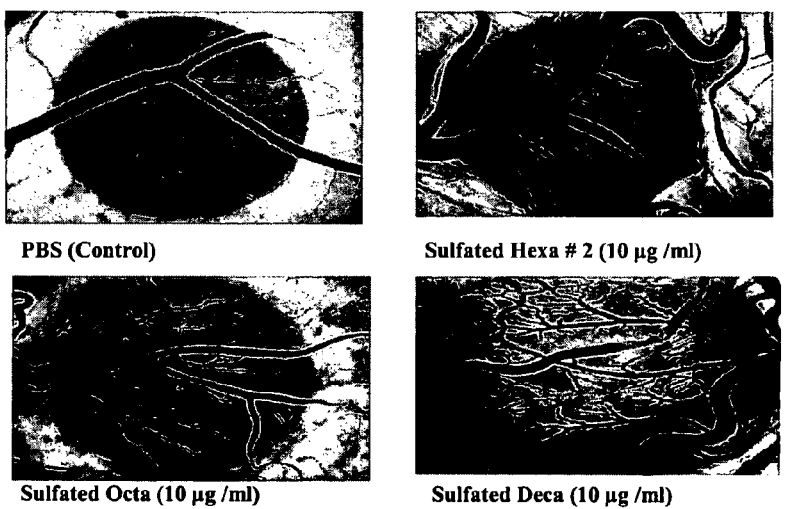
FIG. 20 Effects of Low Molecular Weight Sulfated saccharides on angiogenesis in the chick CAM model.

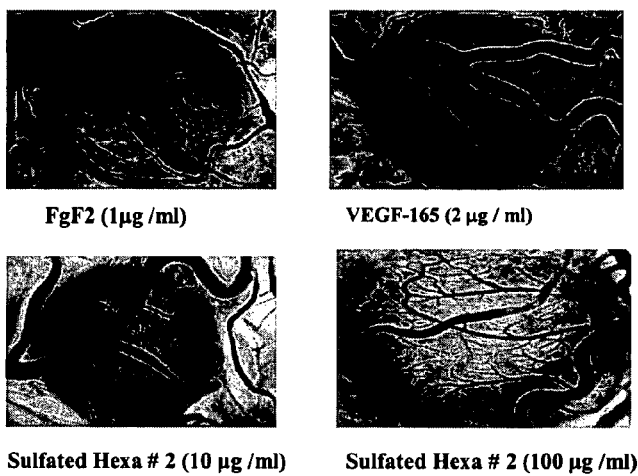
FIG. 21 Comparison of the pro-angiogenesis effects of Low Molecular Weight Sulfated saccharides versus FGF2 or VEGF.

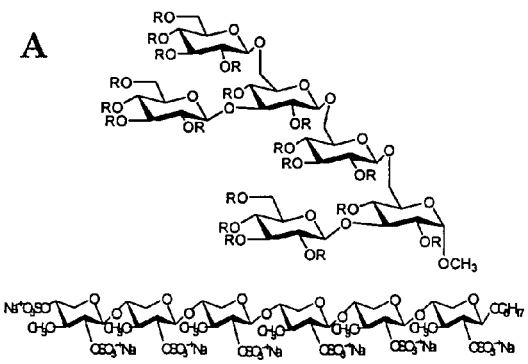
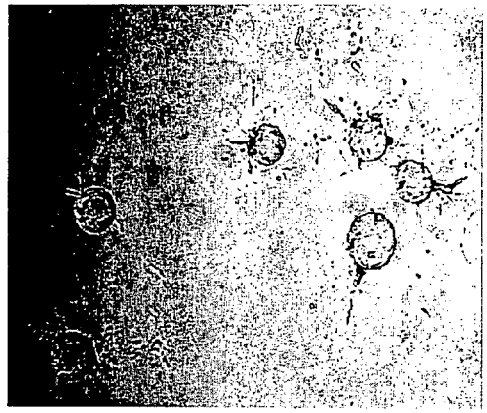
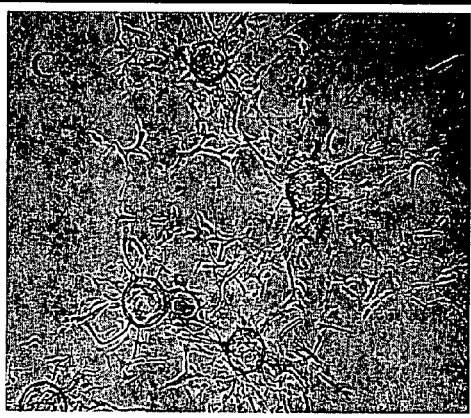
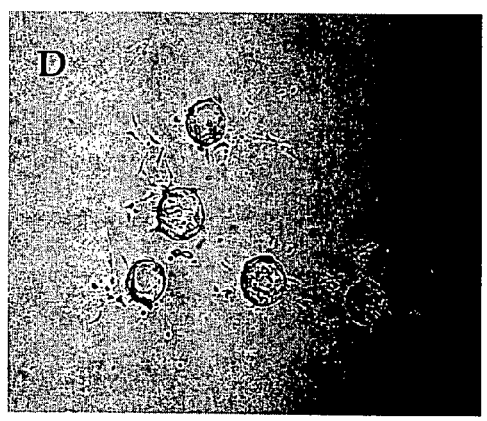
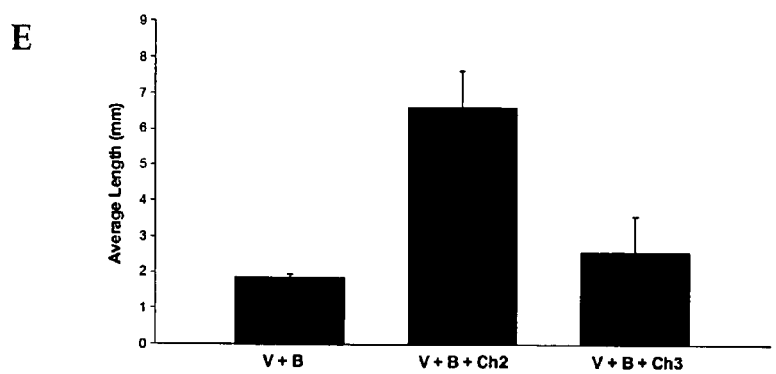
FIG. 24

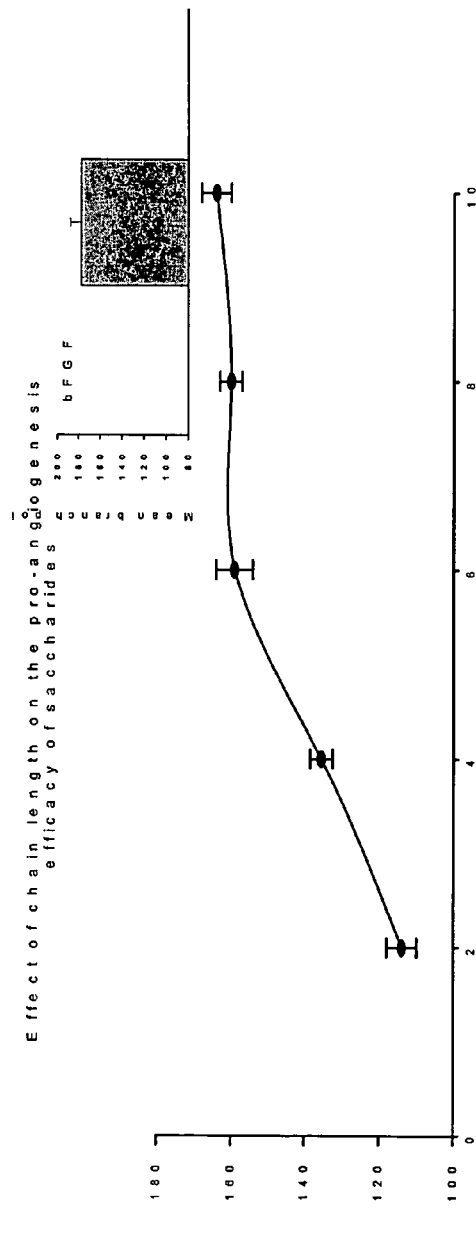
FIG. 28
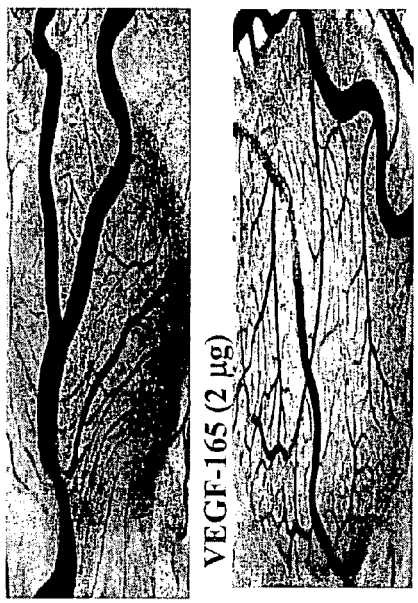
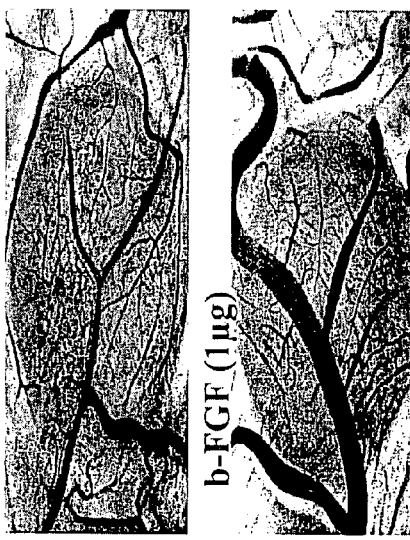
FIG. 29

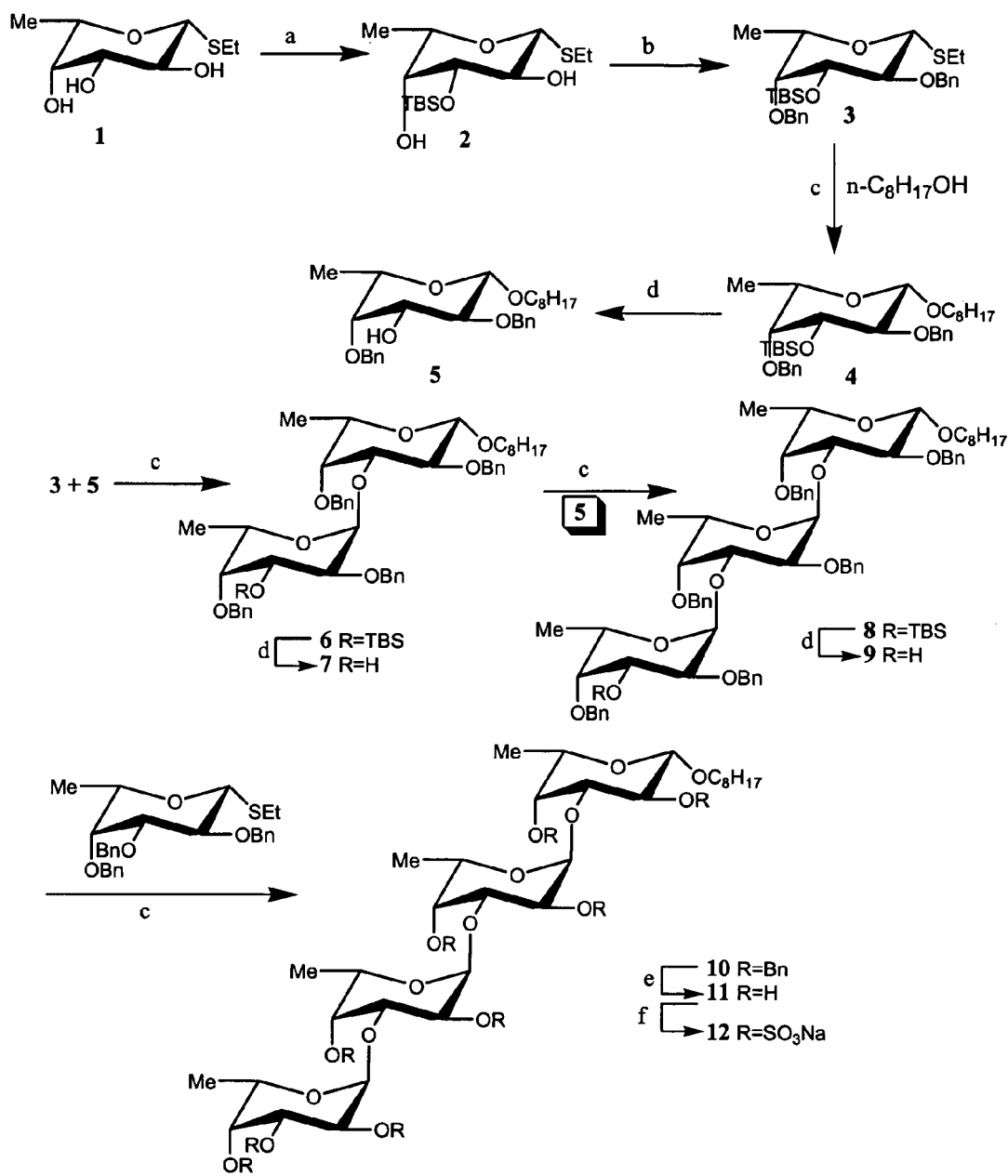
Fig. 30 – Scheme 1

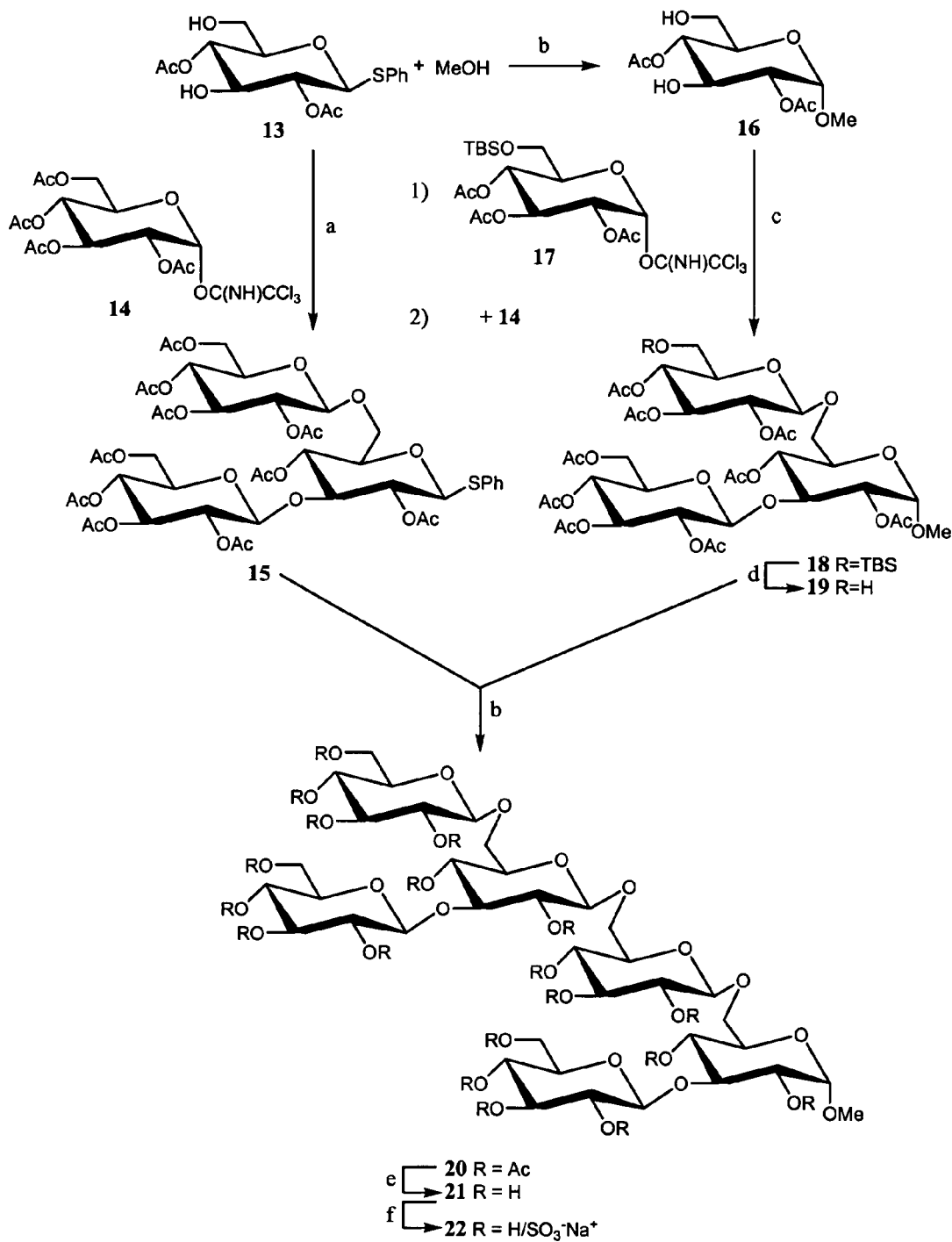
FIG. 31 - Scheme 2

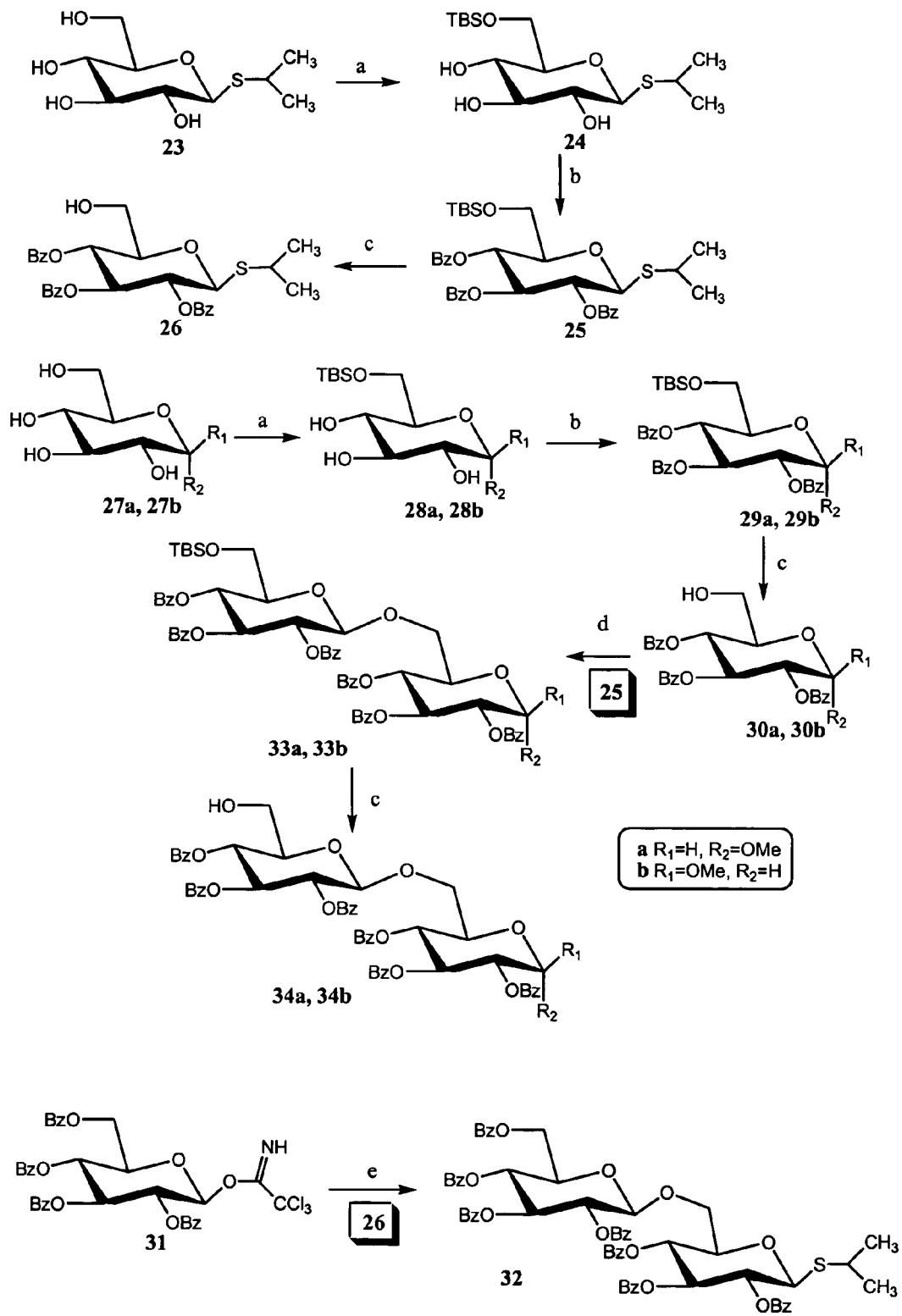
FIG. 32 A - Scheme 3

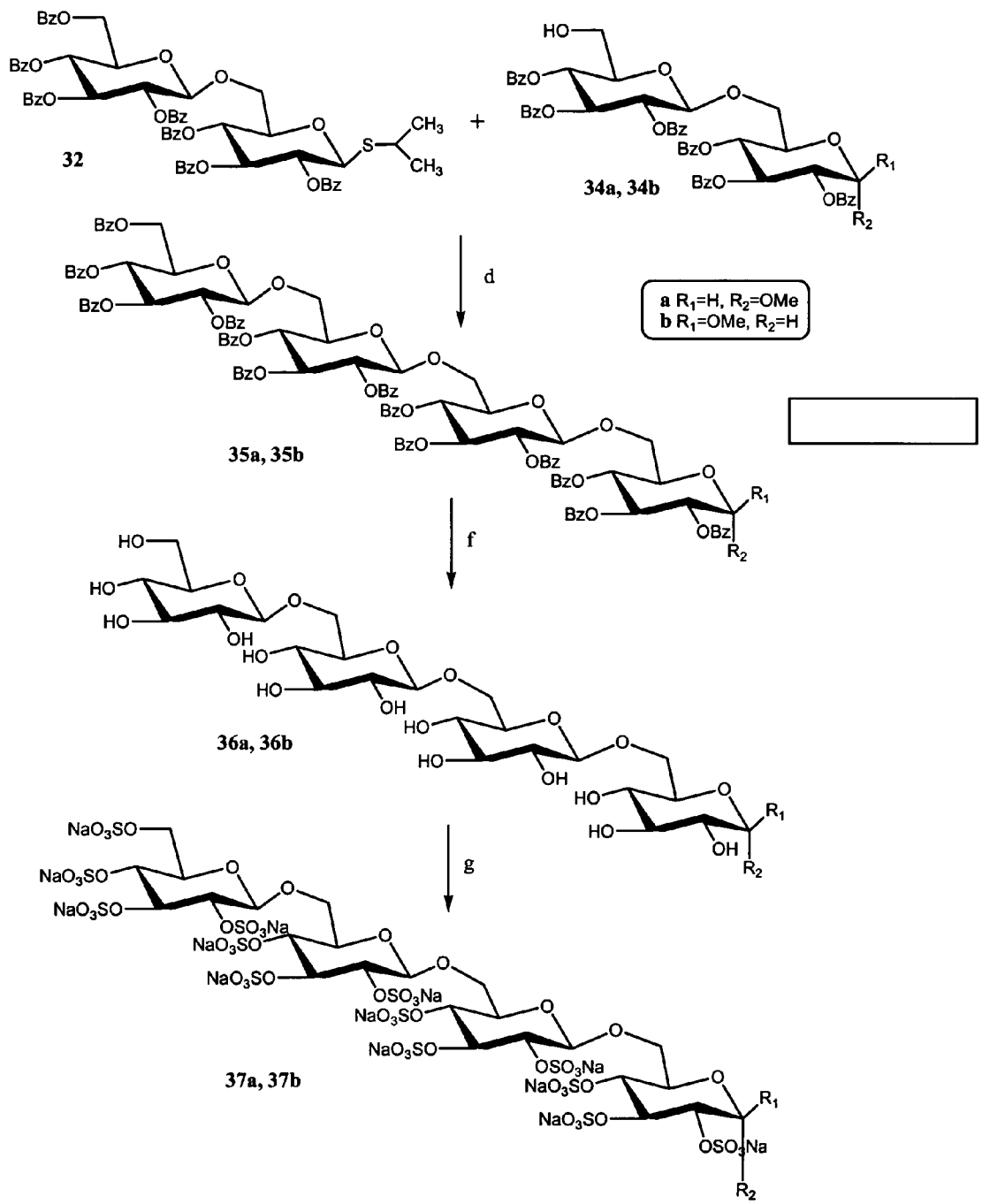
FIG. 32 B - Scheme 3

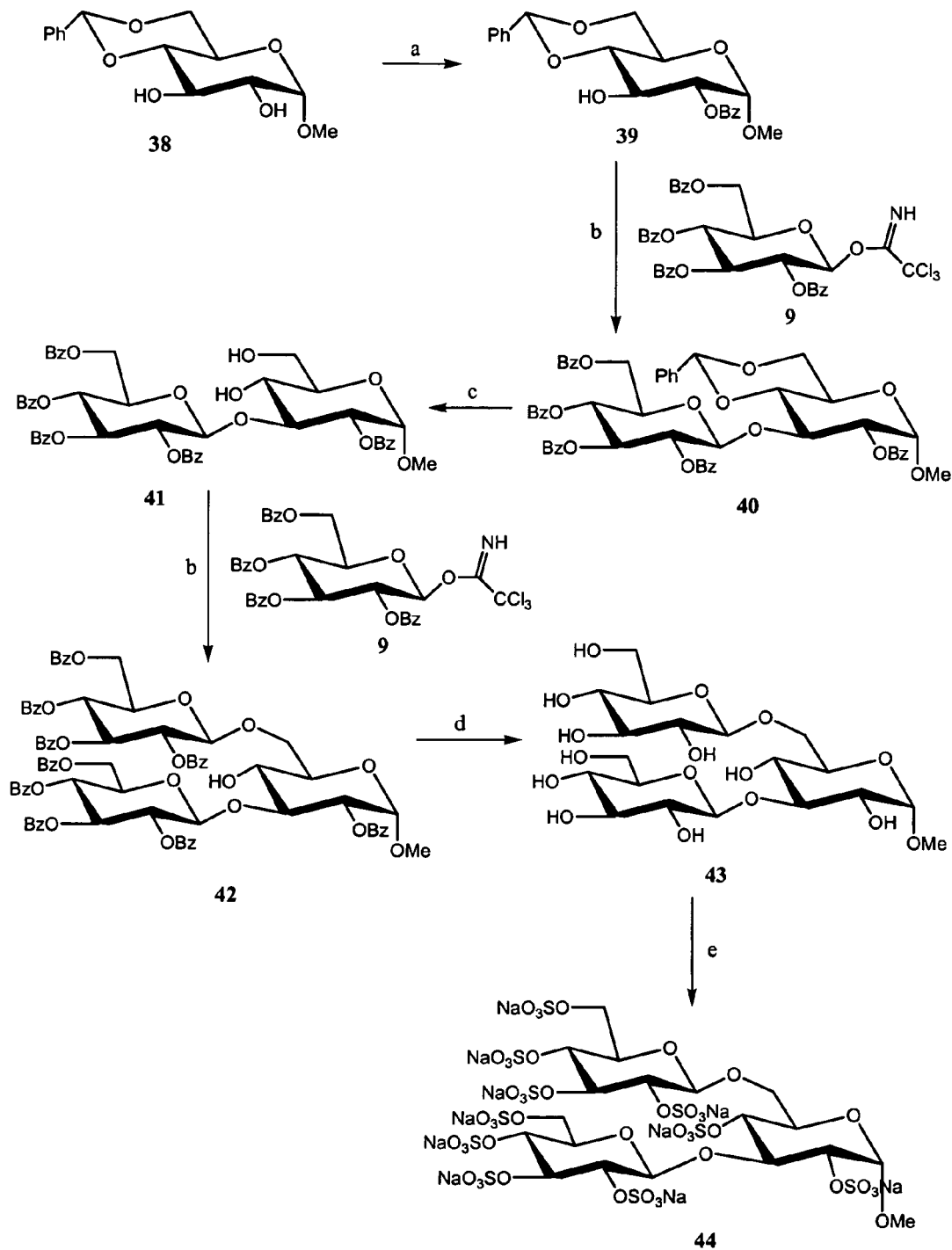
FIG. 33 Scheme 4

COMPOSITION AND METHOD FOR TREATING OCCLUSIVE VASCULAR DISEASES, NERVE REGENERATION, AND WOUND HEALING

RELATED APPLICATION

The present invention claims priority to U.S. Provisional Application No. 60/641,293, filed on Jan. 3, 2005, which is incorporated herein in its entirety.

BACKGROUND OF THE INVENTION

1. Technical Field

The present invention relates to compositions and methods for treatment of wound healing, occlusive peripheral vascular, carotid, coronary disease, neuroprotection, nerve regeneration in spinal cord injury, stroke, Alzheimer, and in diabetic neuropathy are disclosed.

2. Related Art

It is estimated that five million people are afflicted with chronic stable angina in the United States. Each year 200,000 people under the age of 65 die with what is termed "premature ischemic heart disease." Despite medical therapy, many go on to suffer myocardial infarction and debilitating symptoms prompting the need for revascularization with either percutaneous transluminal coronary angioplasty or coronary artery bypass surgery. Medical researchers have postulated that one way of relieving myocardial ischemia would be to enhance coronary collateral circulation.

Fujita et. al. (Fujita et al., Am. Heart Journal., 122:453 (1991), Fujita et al., Int. J. Cardiol., 40:51 (1993) demonstrated that standard heparin in combination with short-term exercise training improved exercise tolerance as measured by dynamic exercise testing. The researchers, believing this effect was mediated through increased collateral vascular development, examined the effects of heparin in combination with a brief concomitant exercise training protocol on coronary collateral flow. Thallium-201 myocardial perfusion images were obtained in association with the same workload both before and late after combined heparin exercise treatment, which indicated that coronary collateral circulation was enhanced. Such dramatic changes over a short term do not occur naturally, and suggest that angiogenesis has taken place.

Correlations have now been made between the anatomic appearance of coronary collateral vessels ("collaterals") visualized at the time of intracoronary thrombolitic therapy during the acute phase of myocardial infarction and the creatine kinase time-activity curve, infarct size, and aneurysm formation. These studies demonstrate a protective role of collaterals in hearts with coronary obstructive disease, showing smaller infarcts, less aneurysm formation, and improved ventricular function compared with patients in whom collaterals were not visualized.

When the cardiac myocyte is rendered ischemic, collaterals develop actively by growth with DNA replication and mitosis of endothelial and smooth muscle cells. One hypothesis suggests that heparin-binding growth factors are present in the heart, or that biological activity is quiescent under normal physiological conditions. Once ischemia develops, these factors are activated and become available for receptor occupation, which may initiate angiogenesis after exposure to exogenous heparin. Unfortunately, the "natural" process by which angiogenesis occurs is inadequate to reverse the ischemia in almost all patients with coronary artery disease.

During ischemia, adenosine is released through the breakdown of ATP. Adenosine participates in many cardio-protective biological events. Adenosine has a role in hemodynamic changes such as bradycardia and vasodilation, and adenosine has been suggested to have a role in such unrelated phenomena as preconditioning and possibly the reduction in reperfusion injury (Ely and Berne, Circulation, 85: 893 (1992).

Intrinsic adenosine may facilitate the coronary flow response to increased myocardial oxygen demands and so modulate the coronary flow reserve. Ethier et. al. (Am. J. Physiol., H131 (1993) demonstrated that the addition of physiological concentrations of adenosine to human umbilical vein endothelial cell cultures stimulates proliferation, possibly via a surface receptor. They suggested that adenosine may be a factor for human endothelial cell growth and possibly angiogenesis. Angiogenesis appears to be protective for patients with coronary artery disease (CAD), but the rate at which blood vessels grow naturally is inadequate to reverse the disease. Thus, strategies to enhance and accelerate the body's natural angiogenesis potential should be beneficial in patients with CAD.

There remains a need for an effective therapy for promotion of angiogenesis and neurogenesis with minimum side effects. Such a therapy would be particularly useful for patients who have myocardial infarctions and could be used prophylactically in patients who have poor coronary circulation, which places them at high risk of ischemia and myocardial infarctions.

During the past decade, vascular endothelial growth factor (VEGF) has been widely investigated, and reported to have pleiotropic functions in the central nervous system (CNS) and its supporting physiological environment. VEGF is involved in not only such well-known functions as angiogenesis, accentuation of vessel permeability, and glial proliferation, but also more recently acknowledged functions such as neuroprotection and even neurogenesis itself. Most recently, the neurogenesis function has attracted much attention, and a number of research groups have taken up the challenge of elucidating this activity. In keeping with this trend, our knowledge of VEGF receptors has increased, and certain suggestions concerning the mechanisms of neuroprotection have come to light in the course of the ongoing work, though at times what the researchers had to work with was only a tiny percent of the signal transduction of VEGF. Together with flt-1 (VEGF receptor 1) and flk-1 (VEGF receptor 2), neuropilin (NP) is frequently described as being involved in the neuroprotective effects of VEGF. In this review, both the direct and indirect neuroprotective effects of VEGF, including various signaling pathways as well as the neurogenesis induced by this factor, are discussed in the context of the newly emerging insights into the biological mechanisms of VEGF and closely related, interacting molecules (Yasuhara T, et al: Rev Neurosci. 2004; 15(4):293-307).

Degeneration of brain tissue following stroke leads to functional impairment with limited brain self-repair. New evidence suggests that delivery of circulating CD34(+) human umbilical cord blood cells can produce functional recovery in an animal stroke model with concurrent angiogenesis and neurogenesis leading to some restoration of cortical tissue (Peterson D A: J Clin Invest. 2004; 114(3):312-314).

SUMMARY OF THE INVENTION

The present invention provides a composition, comprising a sulfated saccharide conjugated to a polymer, said sulfated saccharide having a molecular weight less than 5000 Dalton.

The present invention provides a method for treating a subject with respect to a pathological condition comprised by a subject, said method comprising administering a composition to the subject, said composition comprising a sulfated saccharide having a molecular weight less than 5000 Dalton.

The present invention provides a method for treating a subject with respect to a pathological condition comprised by a subject, said method comprising administering a composition to the subject, said composition comprising a sulfated saccharide conjugated to a polymer, said sulfated saccharide having a molecular weight less than 5000 Dalton.

BRIEF DESCRIPTION OF DRAWINGS

FIG. 1 depicts a Nuclear Magnetic Resonance (NMR) plot for sulfated fucose tetrasaccharide, in accordance with embodiments of the present invention.

FIG. 2 depicts a Mass Spectra (MS) plot for sulfated fucose tetrasaccharide, in accordance with embodiments of the present invention.

FIG. 3 depicts a NMR plot for compound 21 of FIG. 31, in accordance with embodiments of the present invention.

FIG. 4 depicts a MS plot for compound 21 of FIG. 31, in accordance with embodiments of the present invention.

FIG. 5 depicts a NMR plot for compound 22 of FIG. 31, in accordance with embodiments of the present invention.

FIG. 6 depicts a MS plot for compound 22 of FIG. 31, in accordance with embodiments of the present invention.

FIG. 7 depicts a NMR plot for a compound 36a of FIG. 32B, in accordance with embodiments of the present invention.

FIG. 8 depicts a NMR plot for a compound 36b of FIG. 32B, in accordance with embodiments of the present invention.

FIG. 9 depicts a MS plot for a compound 36a of FIG. 32B, in accordance with embodiments of the present invention.

FIG. 10 depicts a MS plot for a compound 36b of FIG. 32B, in accordance with embodiments of the present invention.

FIG. 11 depicts a NMR plot for a compound 37a of FIG. 32B, in accordance with embodiments of the present invention.

FIG. 12 depicts a NMR plot for a compound 37b of FIG. 32B, in accordance with embodiments of the present invention.

FIG. 13 depicts a MS plot for a compound 37a of FIG. 32B, in accordance with embodiments of the present invention.

FIG. 14 depicts a MS plot for a compound 37b of FIG. 32B, in accordance with embodiments of the present invention.

FIG. 15 depicts a NMR plot for a compound 43 of FIG. 33, in accordance with embodiments of the present invention.

FIG. 16 depicts a MS plot for a compound 43 of FIG. 33, in accordance with embodiments of the present invention.

FIG. 17 depicts a NMR plot for a compound 44 of FIG. 33, in accordance with embodiments of the present invention.

FIG. 18 depicts a MS plot for a compound 44 of FIG. 33, in accordance with embodiments of the present invention.

FIG. 19 depicts an in vitro sprout angiogenesis model, in accordance with embodiments of the present invention.

FIG. 20 depicts stimulation of angiogenesis by sulfated saccharides, in accordance with embodiments of the present invention.

FIG. 21 depicts stimulation of angiogenesis by sulfated hexasaccharide versus FGF2 or VEGF, in accordance with embodiments of the present invention.

FIG. 24 depicts a comparison of branched versus linear sulfated synthetic oligosaccharides three-dimensional in vivo angiogenesis assay in the presence of VEGF and b-FGF, in accordance with embodiments of the present invention.

FIG. 28 depicts effect of heparin oligosaccharide chain length on pro-angiogenesis in the in vivo CAM model, in accordance with embodiments of the present invention.

FIG. 29 depicts representative illustration for the pro-angiogenesis effect of sulfated saccharide analogs versus b-FGF or VEGF in the CAM mode, in accordance with embodiments of the present invention.

FIG. 30 depicts Scheme 1 for synthesizing sulfated fucose tetrasaccharide, in accordance with embodiments of the present invention.

FIG. 31 depicts Scheme 2 for synthesizing hexa-β-D-glucopyranoside, in accordance with embodiments of the present invention.

FIGS. 32 A and 32B depicts Scheme 3 for synthesizing tetra-β-D-glucopyranosides, in accordance with embodiments of the present invention.

FIG. 33 depicts Scheme 4 for synthesizing tri-β-D-glucopyranoside, in accordance with embodiments of the present invention.

DETAILED DESCRIPTION OF THE INVENTION

Figure 22:
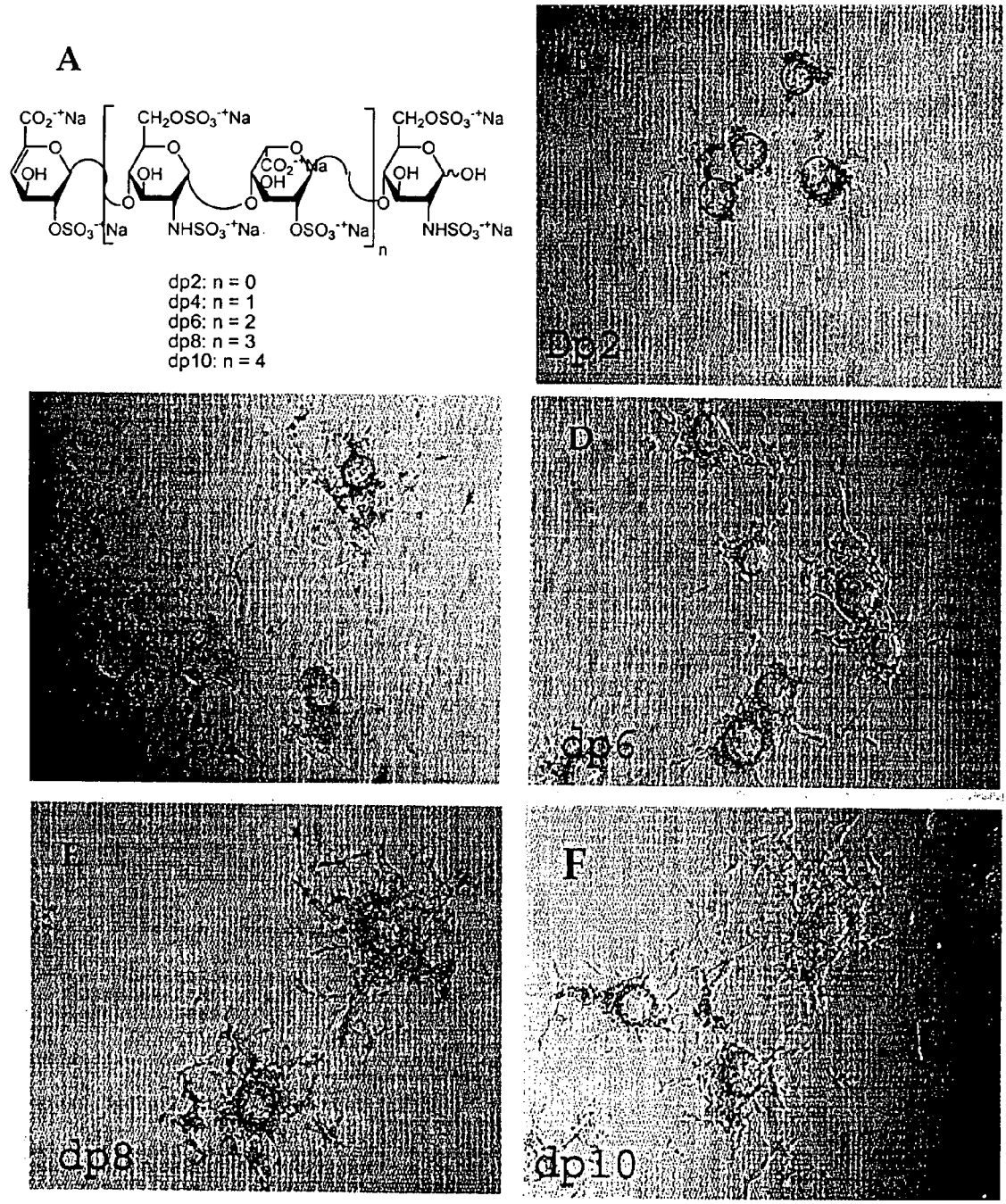
FIG. 22 depicts in vitro angiogenesis assay of structurally defined, homogenous heparin-derived oligosaccharides in the presence of VEGF and b-FGF, in accordance with embodiments of the present invention.

As used herein, the term "angiogenic agent" includes any compound or substance that promotes or encourages angiogenesis, whether alone or in combination with another substance. Examples include, but are not limited to Low Molecular Weight Sulfated saccharides analogs, or polymeric analogs. Low Molecular Weight is defined herein as a molecular weight less than 5000 Dalton.

As used herein, the term "myocardial ischemia" is defined as an insufficient blood supply to the heart muscle caused by a decreased capacity of the heart vessels. As used herein, the term "coronary disease" is defined as diseases/disorders of cardiac function due to an imbalance between myocardial function and the capacity of coronary vessels to supply sufficient blood flow for normal function. Specific coronary diseases/disorders associated with coronary disease which can be treated with the compositions and methods described herein include myocardial ischemia, angina pectoris, coronary aneurysm, coronary thrombosis, coronary vasospasm, coronary artery disease, coronary heart disease, coronary occlusion and coronary stenosis.

As used herein the term "occlusive peripheral vascular disease" (also known as peripheral arterial occlusive disorder) is a vascular disorder-involving blockage in the carotid or femoral arteries, including the iliac artery. Occlusive vascular diseases include but not limited to conditions in Sickle cell patients. Blockage in the femoral arteries causes pain and restricted movement. A specific disorder associated with occlusive peripheral vascular disease is diabetic foot, which affects diabetic patients, often resulting in amputation of the foot.

As used herein the terms "regeneration of blood vessels," "angiogenesis," "revascularization," and "increased collateral circulation" (or words to that effect) are considered as synonymous. The term "pharmaceutically acceptable" when referring to a natural or synthetic substance means that the substance has an acceptable toxic effect in view of its much greater beneficial effect, while the related term, "physiologically acceptable," means the substance has relatively low toxicity. The term, "co-administered" means two or more drugs are given to a patient at approximately the same time or in close sequence so that their effects run approximately concurrently or substantially overlap. This term includes sequential as well as simultaneous drug administration.

"Pharmaceutically acceptable salts" refers to pharmaceutically acceptable salts of Low Molecular Weight Sulfated saccharides (molecular weight<5000 Dalton) analogs, polymeric forms, and derivatives, which salts are derived from a variety of organic and inorganic counter ions well known in the art and include, by way of example only, sodium, potassium, calcium, magnesium, ammonium, tetra-alkyl ammonium, and the like; and when the molecule contains a basic functionality, salts of organic or inorganic acids, such as hydrochloride, hydro-bromide, tartrate, mesylate, acetate, maleate, oxalate and the like can be used as the pharmaceutically acceptable salt.

"Subject" includes living organisms such as humans, monkeys, cows, sheep, horses, pigs, cattle, goats, dogs, cats, mice, rats, cultured cells, and transgenic species thereof. In an embodiment, the subject is a human being. Administration of the compositions of the present invention to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation.

"Administering" includes routes of administration which allow the compositions of the invention to perform their intended function, e.g., promoting angiogenesis. A variety of routes of administration are possible including, but not necessarily limited to parenteral (e.g., intravenous, intra-arterial, intramuscular, subcutaneous injection), oral (e.g., dietary), topical, nasal, rectal, or via slow releasing micro-carriers depending on the disease or condition to be treated. Oral, parenteral and intravenous administration is preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvant and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See generally, *Remington's Pharmaceutical Science,* 16th Edition, Mack, Ed. (1980).

"Effective amount" includes those amounts of pro-angiogenic compounds which allow it to perform its intended function, e.g., promoting angiogenesis in angiogenesis-related disorders as described herein. The effective amount will depend upon a number of factors, including biological activity, age, body weight, sex, general health, severity of the condition to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, e.g., in *Remington's Pharmaceutical Sciences*.

The present invention provides compositions and methods for treatment of wound healing, occlusive peripheral vascular, carotid, coronary disease, neuroprotection, nerve regeneration in spinal cord injury, stroke, and in diabetic neuropathy are disclosed. The compositions and methods allow treatment of diseases associated with occlusion of coronary vessels, for example, by promoting growth of new blood vessels, i.e., angiogenesis and/or by recruitment of collaterals. A series of novel sulfated saccharides synthesized recently were found having pro-angiogenesis activities, making these potential candidates to treat diseases caused by insufficient angiogenesis and/or neuronal injury or neuropathy. The methods involve the administration of polymeric forms, hydrogel of Low Molecular Weight sulfated saccharides (molecular weight<5000 Dalton) alone or in combination with other pro-angiogenesis agents, neuroprotective agents, and/or vasodilators over a period of several weeks. In particular, this invention is applicable to improving wound healing, collateral coronary, peripheral artery, and carotid circulation in patients suffering from impaired wound healing, neuropathy, impotence, erectile dysfunction, myocardial infarction, peripheral artery diseases, spinal cord injury, nerve injury, and other vascular occlusive disorders such as sickle cell disease, and stroke.

A series of novel sulfated oligosaccharides were synthesized recently by the inventors of the present invention and were found having pro-angiogenesis activities, making these analogs a potential candidates to treat diseases caused by insufficient angiogenesis. The invention is based, in part, on the discovery that Low Molecular Weight Sulfated saccharides (molecular weight<5000 Dalton) or sulfated oligosaccharides, and their polymeric forms have pro-angiogenesis properties. Accordingly, these Low Molecular Weight Glycosamino glycans mimics, and polymeric forms (i.e., pro-angiogenesis agents) can be used to treat a variety of deficient angiogenesis-mediated disorders.

Accordingly, one aspect the present invention features methods for treating a condition amenable to treatment by promoting angiogenesis by administering to a subject in need thereof an amount of a polymeric form of Low Molecular Weight Glycosamino glycans, or an analog thereof, effective for promoting angiogenesis. Examples of such conditions amenable to treatment by promoting angiogenesis are provided herein and can include occlusive vascular disease, sickle cell diseases, coronary disease, erectile dysfunction, myocardial infarction, ischemia, stroke, peripheral artery vascular disorders, and wounds.

Over 150 million men worldwide suffer from erectable dysfunction and only a small percentage is being treated for it. Although a number of diseases such as diabetes can be the cause, in most cases the underlying problem can't be identified. Viagra® was the first oral drug to be approved by the U.S. Food and Drug Administration for erectility dysfunction. Since its approval, over 17 million men have received Viagra® worldwide. Other manufacturers are rushing products through clinical trials to compete with Viagra®. Viagra®, Levitra® and Cialis® all work to reduce the effects of an enzyme called PDE5. Reducing the activity of the PDE5 enzyme means more blood can flow to the penis and less leaves. A combined use of Low Molecular Weight Glycosamino glycans, derivatives, or polymer conjugate topically or systemically with hormonally inactive analogs that sustain potent pro-angiogenesis effects would be of value in enhancing the effects of other standard therapies such as listed above, vasodilators, and others.

Examples of Low Molecular Weight Sulfated saccharides (molecular weight<5000 Dalton) or conjugated to polyvinyl alcohol, acrylic acid ethylene co-polymer, poly-Lactic acid, or polyethylene glycol on the carboxylic acid terminal are also provided herein. The conjugation is via covalent or non-covalent bonds depending on the polymer used. The polymer may be biodegradable or non-biodegradable.

In one embodiment the Low Molecular Weight Glycosamino glycan mimics or polymeric forms thereof are administered by parenteral, oral, rectal, or topical means, or combinations thereof. Parenteral modes of administration include, for example, subcutaneous, intraperitoneal, intramuscular, or intravenous modes, such as by catheter. Topical modes of administration can include, for example, a band-aid.

In another embodiment, Low Molecular Weight Glycosamino glycans, or polymeric forms thereof can be encapsulated or incorporated in a microparticle, liposome, or polymer. The polymer can include, for example, polyglycolide, polylactide, or co-polymers thereof. The nano-particle has a size (i.e., linear dimension) of about less than 200 nanometers, and can be administered via one or more parenteral routes, or other mode of administration. In another embodiment the liposome or microparticle can be lodged in capillary beds surrounding ischemic tissue, or applied to the inside of a blood vessel via a catheter. Furthermore, branched sulfated saccharides could be conjugated to dendrimers. Dendrimers are hyper-branched synthetic macromolecules that can be made using controlled sequential processes to give them defined structural and molecular weight characteristics. There is increasing recognition of the importance of polyvalent receptor-ligand interactions between carbohydrates and proteins in many aspects of cell surface mediated immunoregulation. The chemical functionality of dendrimer end groups can be modified to make molecules with novel biological properties that exploit polyvalent and cooperative receptor-ligand interaction.

Low Molecular Weight Glycosamino glycans referred to as sulfated saccharides, sulfated oligosaccharides, or their polymeric forms thereof according to the invention can also be co-administered with one or more biologically active substances that can include, for example, growth factors, vasodilators, anti-coagulants, anti-virals, anti-bacterials, anti-inflammatories, immuno-suppressants, analgesics, vascularizing agents, or cell adhesion molecules, or combinations thereof. In one embodiment, the Low Molecular Weight Sulfated saccharides (molecular weight<5000 Dalton) or polymeric form is administered as a bolus injection prior to or post-administering one or more biologically active substance.

Low Molecular Weight Sulfated saccharides based on this invention provides methods for treating vascular occlusive diseases including venous and arterial disorders ranging from venous thromboembolic disorders (deep vein thrombosis, sickle cell diseases, and pulmonary embolism), and arterial thromboembolic disorders (coronary artery diseases, cerebrovascular disorders, and peripheral artery diseases). Low Molecular Weight Sulfated saccharides can be used alone or in conjunction with other standard therapies for vascular disorders.

Growth factors can include, for example, basic fibroblast growth factor, vascular endothelial growth factor, epithelial growth factor, nerve growth factor, platelet-derived growth factor, and vascular permeability factor. Vasodilators can include, for example, adenosine, adenosine derivatives, or combinations thereof. Anticoagulants include, but are not limited to, heparin, heparin derivatives, anti-factor Xa, anti-thrombin, aspirin, clopidgrel, or combinations thereof.

In another aspect of the invention, methods are provided for promoting angiogenesis along or around a medical device by coating the device with Low Molecular Weight Glycosamino glycans, or polymeric form thereof according to the invention prior to inserting the device into a patient. The coating step can further include coating the device with one or more biologically active substance, such as, but not limited to, a growth factor, a vasodilator, an anti-coagulant, or combinations thereof. Examples of medical devices that can be coated with Low Molecular Weight Sulfated saccharides (molecular weight<5000 Dalton) or polymeric forms according to the invention include stents, catheters, cannula or electrodes.

In yet a further aspect, the invention provides compositions (i.e., pro-angiogenesis agents) that include Low Molecular Weight Glycosamino glycans, and analogs conjugated to a polymer. The conjugation can be through a covalent or non-covalent bond, depending on the polymer. A covalent bond can occur through an ester or anhydride linkage, for example. In one embodiment, the polymer can include, but is not limited to, polyvinyl alcohol, acrylic acid ethylene co-polymer, poly-lactic acid, or polyethylene glycols.

In another aspect, the invention provides for pharmaceutical formulations including the pro-angiogenesis agents according to the present invention in a pharmaceutically acceptable carrier. In one embodiment, the pharmaceutical formulations can also include one or more pharmaceutically acceptable excipients.

The pharmaceutical formulations according to the present invention can be encapsulated or incorporated in a liposome, microparticle, or polymer. The liposome or microparticle has a size of less than about 200 nanometers. Any of the pharmaceutical formulations according to the present invention can be administered via parenteral, oral, rectal, or topical means, or combinations thereof. In another embodiment, the pharmaceutical formulations can be co-administered to a subject in need thereof with one or more biologically active substances including, but not limited to, growth factors, vasodilators, anti-coagulants, or combinations thereof.

Unless defined otherwise, all technical and scientific terms used herein have the same meaning as commonly understood by one of ordinary skill in the art to which this invention belongs. All patents and publications cited in this specification are incorporated by reference in their entirety.

Compositions and methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of polymeric forms of Low Molecular Weight Sulfated saccharides (molecular weight<5000 Dalton) and an effective amount of an adenosine and/or nitric oxide donor. The compositions can be in the form of a sterile, injectable, pharmaceutical formulation that includes an angiogenically effective amount of Low Molecular Weight Sulfated saccharides (molecular weight<5000 Dalton) and adenosine derivatives in a physiologically and pharmaceutically acceptable carrier, optionally with one or more excipients.

The methods involve the co-administration of an effective amount of Low Molecular Weight Sulfated saccharides (molecular weight<5000 Dalton) or polymeric forms and an effective amount of an adenosine and/or NO donor in low, daily dosages for a week or more. One or both components can be delivered locally via catheter. Low Molecular Weight Sulfated saccharides (molecular weight<5000 Dalton) in vivo can be delivered to capillary beds surrounding ischemic tissue by incorporation of the compounds in an appropriately sized liposome or microparticle. Low Molecular Weight Glycosamino glycans, polymeric forms and derivatives can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart, for example, occlusive peripheral vascular disease (also known as peripheral arterial occlusive disease), where decreased blood flow is a problem.

Angiogenesis, defined as the development of new blood vessels from preexisting vessels, is an important natural process occurring in the body, both in health and in disease. In many serious diseases, the body loses control over angiogenesis. Angiogenesis-dependent disease results when new blood vessels either grow excessively or insufficiently. Diseases such as coronary artery disease, stroke, and delayed wound healing are caused by insufficient angiogenesis. Inadequate blood vessels growth, results in circulation that is not properly restored leading to the risk of tissue death. A series of novel sulfated oligosaccharides we synthesized recently were found having pro-angiogenesis activities, making these potentially good drug candidates to treat diseases caused by insufficient angiogenesis.

Described next are chemical structure and method of synthesis of: sulfated fucose tetrasaccharide, hexa-β-D-glucopyranoside, sulfated octyl 3-O-methyl-xylopyranosyl hexasaccharide, tetra-β-D-glucopyranosides, tri-β-D-glucopyranoside, and oligosaccharide.

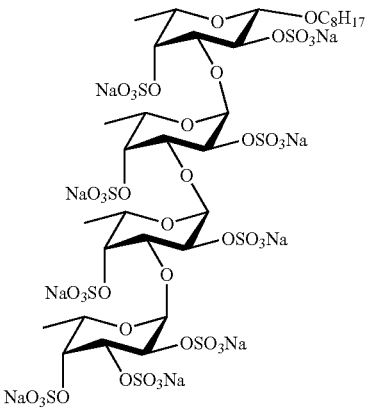

Sulfated Fucose Tetrasaccharide

FIG. 30 depicts Scheme 1 for synthesizing sulfated fucose tetrasaccharide, using the following reagents and conditions (yields): (a) TBSCl, DMF, Im, 0° C. (92%); (b) BnBr, NaH, DMF (97%); (c) NIS, TMSOTf, CH$_2$C$_{12}$, −20° C. (97% for 4; 89% for 6; 80% for 8; 80% for 10); (d) TBAF, THF (89% for 5; 76% for 7; 97% for 9); (e) Pd—C, H$_2$ 1:1 MeOH-EtOAc, 85%; (f) SO$_3$.Pyr, Pyr; 3N NaOH (92%).

The synthesis of sulfated fucose tetrasaccharide according to Scheme 1 in FIG. 30) starts from direct silylation of ethyl 1-thio-β-L-fucopyranoside (1) with tert-butyldimethylsilylchloride (TBSCl) and imidazole in N,N-dimethylformamide (DMF) at 0° C. 92% isolated yield of monosilylated 2 was obtained. Compound 2 was benzylated with BnBr and NaH in DMF to give 3 in 97% yields. Compound 3 was condensed with 1-octanol in CH$_2$Cl$_2$ at −20° C. using N-iodosuccinimide/trimethylsilyl trifluoromethanesulfonate (NIS/TMSOTf) as catalysts to give octyl fucoside (4), followed by tetrabutylammonium fluoride (TBAF)-catalyzed desilylation affording acceptor 5 in 88% isolated yield for two steps. 1H NMR analysis surprisingly found that this major fucoside has the β configuration. Doublet (J 7.7 Hz) at d4.37 ppm (H-1) clearly indicated a β linkage in 5. Glycosylation of 3 and 5 as described in the preparation of 4 gave the α linked disaccharide 6 in 89% yields. 1H-1H COSY of 6 showed a doublet (J 3.9 Hz) at d 5.04 ppm confirming the a linkage between the sugar residues. Reiteration of the desilylation with TBAF and glycosylation with transformed disaccharide 6 into trisaccharide acceptor 9 in 59% overall yield. Final coupling reaction of 9 and benzylated thioglycosyl donor furnished the full benzylated tetrasaccharide 10 (80%). HMQC assigned four anomeric protons that appeared at d 4.30 ppm (J 7.4 Hz), 5.07 ppm (J 3.5 Hz), 5.09 ppm (J 3.4 Hz), and 5.10 ppm (J 3.4 Hz), respectively, supporting the structure of compound 10. Catalytic hydrogenolysis of 10 with H$_2$ on Pd(OH)$_2$ gave the free tetrasaccharide 11, which was subsequently sulfated with the sulfur trioxide-pyridine complex in pyridine at 55° C. for 72 h, giving 12 in an excellent yield (92%) after DOWEX 50WX8 purification and lyophilization of the eluate.

The Nuclear Magnetic Resonance (NMR) data (FIG. 1) and Mass Spectra (MS) data (ESI (−) MS 691.2, [M−2SO$_3$Na$^-$−2Na$^+$+2H$^+$]$^{2-}$) (FIG. 2) confirmed the structure of the sulfated fucose tetrasaccharide compound 12 as shown in FIG. 30—Scheme 1.

FIG. 31 depicts Scheme 2 for synthesizing hexa-β-D-glucopyranoside, using the following reagents and conditions (yields): (a) TMSOTf, CH$_2$Cl$_2$, 0° C., 82%; (b) NIS, TMSOTf, 63% for 16; 86% for 20 (from 18); (c) TMSOTf, CH$_2$Cl$_2$, −42° C.; then TMSOTf, 0° C., 76% (two steps); (d) 95% TFA; (e) NaOMe, MeOH, 93%; (f) SO$_3$.Pyr, DMF.

This hexa-β-D-glucopyranoside was synthesized (Scheme 2—see FIG. 31) starting from phenyl 2,4-di-O-acetyl-1-thio-β-D-glucopyranoside (13). Compound 13 was condensed with glycosyl donor 2,3,4,6-tetra-O-acetyl-a-D-glucopyranosyl trichloroacetimidate (14) in the presence of trimethylsilyl trifluoromethanesulfonate (TMSOTF) in CH$_2$Cl$_2$ to give trisaccharide 15 in one pot with 82% isolated yield. Three doublets at d 4.43 ppm (J 7.9 Hz), 4.52 ppm (J 8.0 Hz) and 4.54 ppm (J 10.0 Hz) in 1H NMR spectrum of 15 clearly indicated all three α-configuration in this trisaccharide. Thioglycoside 15 was used as a latent glycosyl donor in the final assembly of the target hexasaccharide. Attempt to transfer the partially protected donor 13 into its methyl glycoside derivative using N-iodosuccinimide (NIS) and TMSOTf as catalysts resulted in 16 as a major product (63%). 6-O-silylated trichloroacetimidate 17 (1.1 equiv.) was regioselectively coupled with diol 16 using catalytic amount of TMSOTf (0.07 equiv.) at −42° C. in anhydrous methylene chloride. The second donor 14 (1.5 equiv.) was added into the above mixture at 0° C. 2 h later, affording trisaccharide 18 in 76% yield within another 2 h. An extra amount of TMSOTf (0.01 equiv.) was needed to complete the reaction after the addition of 14. The treatment of 18 with 95% trifluoroacetic acid (TFA) for 1 h gave trisaccharide acceptor 19. The resulting crude product was co-evaporated with toluene three times and then directly used for the next step without further purification. Coupling of 15 and 19 in CH$_2$Cl$_2$ at 0° C. under promotion of NIS and TMSOTf gave hexasaccharide 20 in 86% yield over two steps. 1H-1H COSY, TOCSY, HMBC and HMQC spectra analyses clearly indicated 6H-1s [δ$_H$ 4.29 (H-1$^{III}$), 4.49 (H-1$^{II}$), 4.51 (H-1$^{IV}$), 4.58 (H-1$^{VI}$), 4.61 (H-1$^V$), 4.77 (H-1$^I$) ppm] and 6 C-1s [δ$_C$ 96.4 (C-1$^I$), 100.6 (C-1$^{III}$, C-1$^V$), 100.8 (C-1$^{VI}$, C-1$^{IV}$), 100.9 (C-1$^{II}$) ppm], confirming the correct linkages of 20. Standard Zemplén deacetylation of 20 furnished hexa-β-D-glucopyranoside 21 as an amorphous solid (FIG. 31). Compound 21 can be confirmed by NMR (FIG. 3) and MS (FIG. 4, ESI(+)1022.3 ([M+NH$_4^+$]$^+$), ESI (−)1003.3 ([M−H$^+$]$^-$)). Sulfation of 21 with SO$_3$.Pyr (10 equiv.) at 50° C. in N,N-dimethylformamide (DMF) for 3 days, followed by conversion to the sodium salt, removal of pyridine and purification on a DOWEX 50WX8 column, gave a mixture of sulfated 22 as shown in FIG. 31—Scheme 2. The microanalysis for 22 was C, 16.22%; H, 1.73%; and S, 19.90%. This result together with NMR data and MS data for compound 22 (FIG. 5 and FIG. 6, ESI(−)2941.0 ([M−H$^+$]$^+$), 855.5 ([M−3SO$_3$Na$^-$−3Na$^+$+3H$^+$]$^{3-}$) confirmed the presence of fully sulfated hexasaccharide in 23.

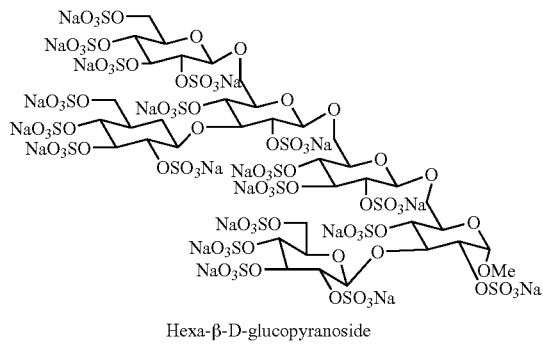

Hexa-β-D-glucopyranoside

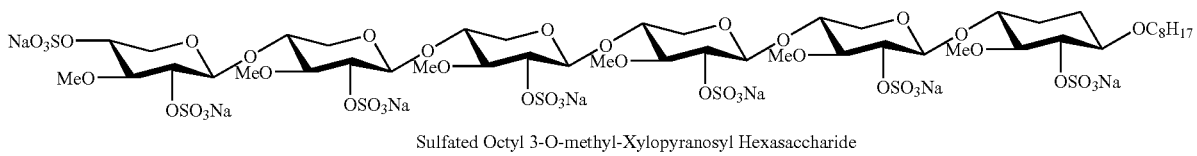

Sulfated Octyl 3-O-methyl-Xylopyranosyl Hexasaccharide

-continued

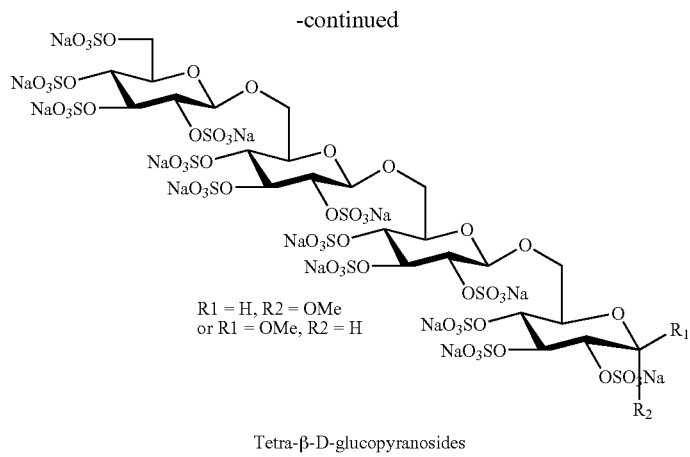

R1 = H, R2 = OMe
or R1 = OMe, R2 = H

Tetra-β-D-glucopyranosides

FIGS. 32 A and 32B (collectively, "FIG. 32") depicts Scheme 3 for synthesizing tetra-β-D-glucopyranosides, using the following reagents and conditions (yields): (a) TBSCl, DMF, Im, 0° C. (92% for 24; 90% for 28); (b) BzCl, Py (86% for 25; 89% for 29); (c) AcCl, CH$_3$OH/CH$_2$Cl$_2$ (84% for 26; 93% for 30; 82% for 34); (d) NIS, TMSOTf, CH$_2$Cl$_2$, 0° C. (90% for 33; 80% for 35); (e) TMSOTf, CH$_2$Cl$_2$, 0° C. (89% for 32); (f) NaOMe, MeOH (91% for 36); (g) SO$_3$.Pyr, Pyridine (96% for 37).

To synthesize the target compounds 37a and 37b (Scheme 3—see FIGS. 32A and 32B), we started from direct silylation of isopropyl 6-O-1-thio-β-D-glucopyranoside (23) with tert-butyldimethylsilyl chloride (TBSCl) and imidazole in dimethylformamide (DMF) at 0° C. which gave 92% yield of 24. Compound 24 was benzoylated with BzCl in pyridine at room temperature to give 25 in 86% yield, then desilylated in CH$_3$OH/CH$_2$Cl$_2$ using acetyl chloride to give 26 in 84% yield. Through the same process, methyl 2,3,4-tri-O-benzoyl-6-D-glucopyranoside (30) was obtained from methyl 2,3,4-6-O-D-glucopyranoside (27). Compound 30 was condensed with compound 25 in CH$_2$Cl$_2$ at 0° C. using N-iodosuccinimide/trimethylsilyl trifluoromethanesulfonate (NIS/TMSOTf) as catalysts to give compound 33 in 90% yield, followed by acetyl chloride-catalyzed desilylation to give disaccharide acceptor 34 in 82% yield. Disaccharide donor 32 was obtained by glycosylation of compound 26 and compound 31$^I$ in CH$_2$Cl$_2$ at 0° C. catalyzed by TMSOTf. Coupling of the donor 32 and the acceptor 34 in CH$_2$Cl$_2$ at 0° C. under promotion of NIS and TMSOTf gave tetrasaccharide 35 in 80% yield. The same desilylation by acetyl chloride converted 35 to 36. NMR spectra in FIG. 7 for 36a and FIG. 8 for 36b), and MS spectra in FIG. 9 for 36a and FIG. 10 for 36b), indicated the structure of compound 36. In proton NMR of compound 36b, doublet peak d 4.36 has J=8.24 Hz, which tells us that the —OCH$_3$ group is in equatorial position. Sulfation of 36 with SO$_3$.Pyr at 55° C. in pyridine for 72 hours, followed by conversion to the sodium salt, removal of pyridine and purification on a DOWEX 50WX8 column, gave the final sulfated tetrasaccharide 37. NMR spectra in FIG. 11 for 37a and FIG. 12 for 37b), and MS spectra in FIG. 13 for 37a and FIG. 14 for 37b), (MOLECULAR WEIGHT<5000 DALTON) indicated the structure of compound 37 as shown in FIG. 32B—Scheme 3.

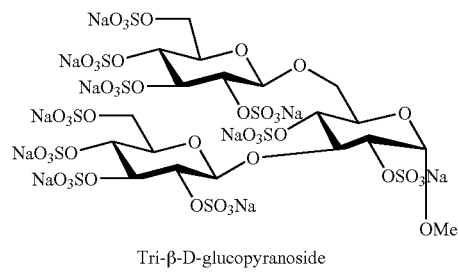

Tri-β-D-glucopyranoside

FIG. 33 depicts Scheme 4 for synthesizing tri-β-D-glucopyranoside, using the following reagents and conditions (yields): (a) BzCl, Py, 0° C. (36% for 39); (b) TMSOTf, CH$_2$Cl$_2$, 0° C. (95% for 40; 63% for 42); (c) 90% TFA, CH$_2$Cl$_2$, (81% for 41); (d) NaOMe, MeOH (80% for 43); (e) SO$_3$.Pyr, Pyridine (92% for 44).

The target trisaccharide was synthesized (Scheme 4—see FIG. 33) from benzoylation of methyl 4,6-di-O-benzylidene-D-glucopyranoside (38) with benzoyl chloride in pyridine at 0° C. Compound 39 was obtained in 36% yield. Compound 39 was glycosylated with compound 31 in CH$_2$Cl$_2$ at 0° C. using TMSOTf as catalysis to give compound 40 in 95% yield. Compound 40 was treated with 90% TFA in dry CH$_2$Cl$_2$ to give disaccharide 41 in 81% yield. Reiteration of the glycosylation with 31 transformed disaccharide 41 into benzoylated trisaccharide 42 in 63% yield. Deprotected benzoyl groups of 42 in MeOH with NaOMe gave the tri-β-D-glucopyranoside 43 in 80% yield. The NMR spectrum (FIG. 15) and MS spectrum (FIG. 16, ESI(+)541.3 ([M+Na$^+$]$^+$), ESI(−)517.7 ([M-H$^+$]$^−$)) confirmed the structure of tri-β-D-glucopyranoside 43. Fully sulfation of compound 43 in pyridine with SO$_3$.Pyr at 55° C. for 72 hours, followed by purification with DOWEX 50×8 column, gave the target compound fully sulfated tri-β-D-glucopyranoside 44. In MS spectrum (FIG. 18), the peaks (ESI (−)746 ([M−2Na$^+$]$^{2−}$), 695 ([M−2Na$^+$−SO$_3$Na$^−$+H$^+$]$^{2−}$) support the existence of fully sulfated tri-β-D-glucopyranoside 44, together with NMR spectrum (FIG. 17), confirmed the structure as shown in FIG. 33—Scheme 4.

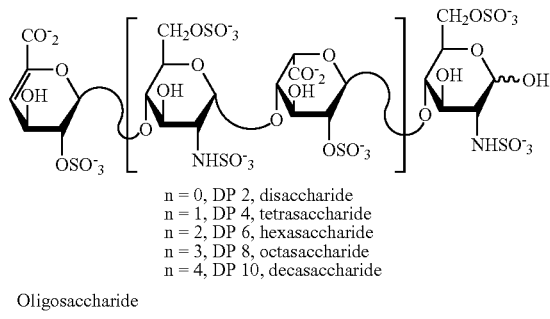

n = 0, DP 2, disaccharide
n = 1, DP 4, tetrasaccharide
n = 2, DP 6, hexasaccharide
n = 3, DP 8, octasaccharide
n = 4, DP 10, decasaccharide Oligosaccharide The heparin oligosaccharide mixture was prepared from bovine lung heparin by controlled enzymatic depolymerization with heparinase. Heparin was digested with heparinase (EC 4.4.2.7) in sodium phosphate buffer (pH 7.0) at 30° C. The reaction mixture was incubated until the digestion was 30% complete, and then the mixture was boiled at 100° C. for 2 min to inactivate the enzyme. The mixture then was pressure filtered with a 5000 MWCO membrane to remove residual heparin and very-high-molecular-weight oligosaccharides. The low-molecular-weight heparin oligosaccharides ($M_r$<5000 Dalton) were fractionated on a Bio Gel P-10 column eluted with sodium chloride and gave the size-uniformed oligosaccharides. The size-uniformed oligosaccharides of degree of polymerization (DP) 2-10 were desalted on a Bio Gel P-2 column and then were separated on semi-preparative SAX-HPLC using sodium chloride linear gradient (0.2 to 2 M in 120 min, pH 3.5). The elution profile was monitored by absorbance at 232 nm and homogeneous oligosaccharides were collected, desalted and freeze-dried.

The effect of different novel synthetic saccharides, with different chain length, different levels of sulfation, different configuration as well as different oligosaccharides derived from Low Molecular Weight Heparin ($M_r$<5,000 Dalton), with different levels of sulfation were determined in angiogenesis modulation.

The effect of low molecular weight sulfated saccharides (molecular weight<5000 Dalton) on micro-vascular endothelial cell sprouting (in Vitro 3D Sprout Angiogenesis) is depicted with respect to culture of HDMEC on micro-carrier beads in FIG. 19. 80% confluent HDMEC (Passage 5-10) are mixed with gelatin-coated Cytodex-3 beads with a ratio of 40 cells per bead. If using 24-well plate for the assay, 150-200 beads per well are used. Cells and beads are suspended with 5 ml EBM+15% normal human serum, mixed gently every one hour for first four hours. Then the mixture culture is left in $CO_2$ incubator overnight. The next morning, 10 ml of fresh EBM+15% HS and culture are added for another three hours. Before experiments, the culture of EC-beads is checked. 500 ul of PBS in a well of 24-well plate is added. 100 ul of the EC-bead culture solution is added to the PBS. The number of beads are observed and counted. The concentration of EC-beads is calculated. The EC-beads are good for experiments for 48 hours.

Fibrinogen solution (1 mg/ml) is prepared in EBM medium with or without angiogenic factors or testing factors. For positive control, 30 ng/ml VEGF+25 ng/ml FGF2 is used. EC-beads are washed with EBM medium for two times and add EC-beads to fibrinogen solution. For each condition, experiment is performed in triplicates. The EC-beads in fibrinogen solution are mixed gently and 2.5 ul human thrombin (0.05 U/ul) in 1 ml fibrinogen solution is added. Then, 300 ul is immediately transferred to each well of 24-well plate.

The fibrinogen solution will polymerize in 5-10 minutes, after 20 mins, add EBM+20% normal human serum+10 ug/ml Aprotinin. The plate is incubated in $CO_2$ incubator. It will take about 24-48 hrs for HDMEC to invade fibrin gel and form tubes.

FIG. 20 illustrates effects of low molecular weight sulfated saccharides on angiogenesis in the chick CAM model. The low molecular weight sulfated saccharides promoted new blood vessel generation in the CAM model as shown in FIG. 20.

FIG. 21 illustrates a comparison of the pro-angiogenesis effects of low molecular weight sulfated saccharides versus FGF2 or VEGF. The low molecular weight sulfated saccharides resulted in comparable pro-angiogenesis effect to that shown with FGF2 or VEGF as shown in FIG. 21.

Low molecular weight sulfated saccharides (molecular weight<5000 DALTON) and sulfated oligosaccharides conjugated with polymers are described next in terms of an ester linkage using polyvinyl alcohol, an anhydride linkage using acrylic acid ethylene co-polymer, or entrapment in a polylactic acid polymer. The sulfated oligosaccharide may range from a tetra to octasaccharide (i.e., the oligosaccharide may be selected from the group consisting of tetraoligosaccharide, a pentaoligosaccharide, a hexaoligosaccharide, a septaoligosaccharide, and an octaoligosaccharide).

FIGS. 34-39 depict various mechanisms for conjugating a sulfated saccharide to a polymer, in accordance with embodiments of the present invention.

Figure 34:
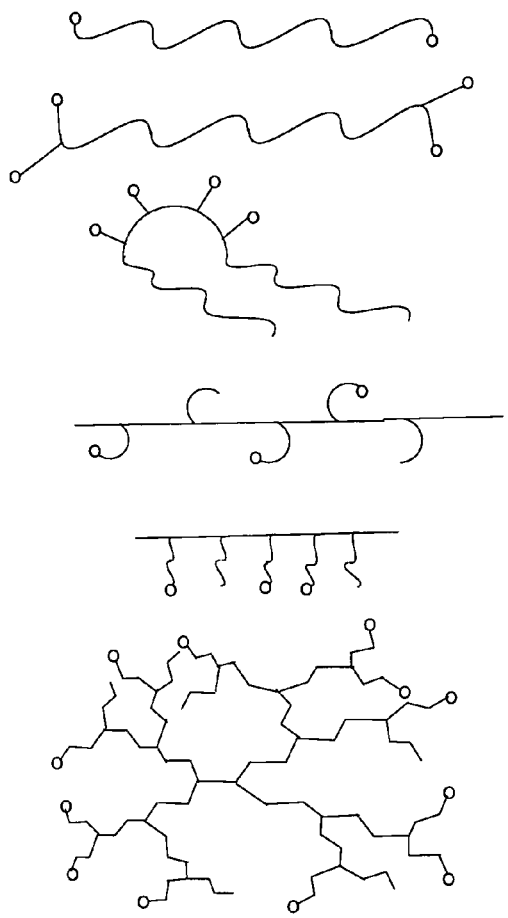
FIG. 34 depicts a general scheme for a compound/entity being conjugated to various polymers with different distributions and orientations of the functional groups, in accordance with embodiments of the present invention.

FIG. 34 depicts a general scheme for a compound/entity being conjugated to various polymers with different distributions and orientations of the functional groups. The O-site of conjugation of the saccharide denote the site of conjugation of the saccharide to the polymer of choice.

Table 1 lists various polymers to which a sulfated saccharide may be conjugated in accordance with the present invention.

TABLE 1

Designated Polymer Conjugates based on Chemical Class Reactivity & Stability Data.

Figure 35A:
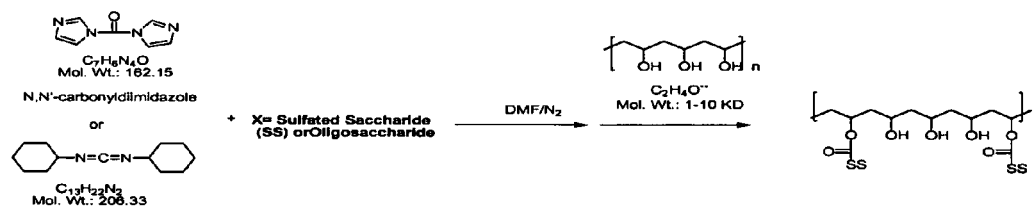
FIGS. 35 A and 35B depict polymer conjugation through an ester linkage wherein polyvinyl alcohol is covalently conjugated to sulfated saccharide/oligosaccharide by reaction of the acid chloride with polyvinyl alcohol, in accordance with embodiments of the present invention.
Figure 35B:
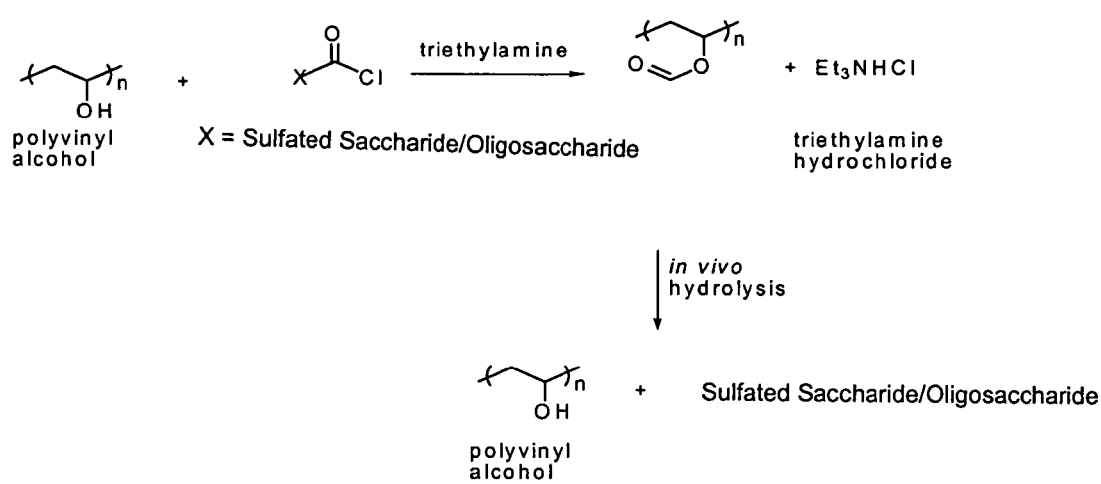

PEG
PEO
m-PEG
PVA
PLLA
PGA
Poly L-Lysine
Hyaluronic Acid
Pectin/Chitosan
Dextran
Collagen
Poly amine
Poly alanine
Polytryptophan
Polytyrosine FIGS. 35A and 35B depict polymer conjugation through an ester linkage wherein polyvinyl alcohol is covalently conjugated (i.e., bonded) to a sulfated saccharide/sulfated oligosaccharide by reaction of the acid chloride with polyvinyl alcohol. In this preparation commercially available polyvinyl alcohol (or related co-polymers) can be esterified by treatment with the acid chloride form of the Low Molecular Weight Glycosamino-glycans. The hydrochloride salt is neutralized by the addition of triethylamine to afford triethylamine hydrochloride which can be washed away with water upon precipitation of the acid analogs peptide ester polymer form for different analogs. The ester linkage to the polymer may undergo hydrolysis in vivo to release the active pro-angiogenesis Low Molecular Weight Glycosamino glycans, sulfated saccharide or sulfated oligosaccharide.

Figure 36:
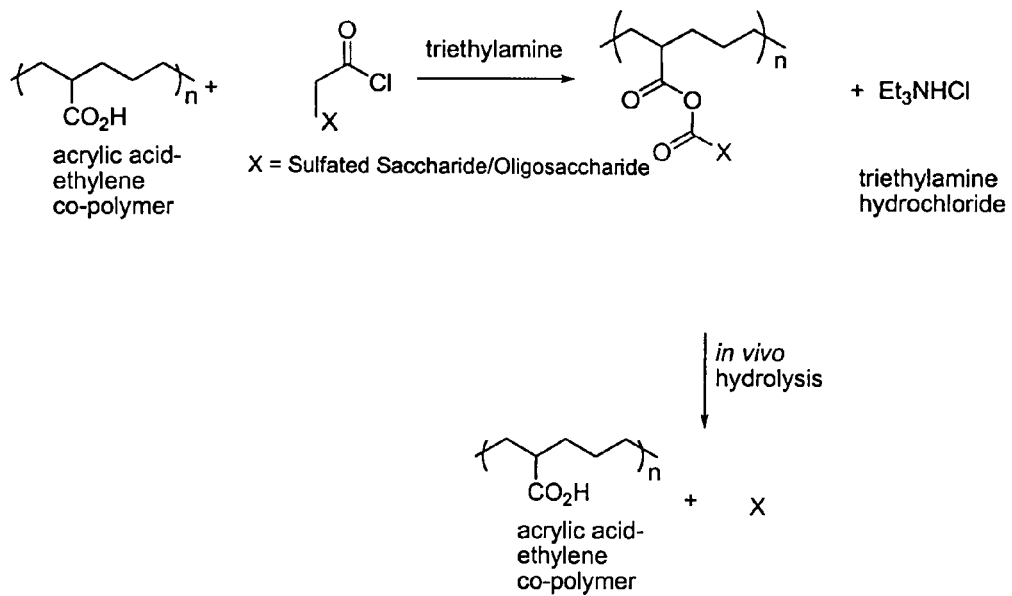
FIG. 36 depicts polymer conjugation through an anhydride linkage, wherein acrylic acid co-polymer is covalently conjugated (i.e., bonded) to a sulfated saccharide/oligosaccharide by reaction of an acrylic acid co-polymer, in accordance with embodiments of the present invention.

FIG. 36 depicts polymer conjugation through an anhydride linkage, wherein acrylic acid co-polymer is covalently conjugated (i.e., bonded) to a sulfated saccharide/sulfated oligosaccharide by reaction of an acrylic acid co-polymer. This anhydride linkage is also susceptible to hydrolysis in vivo to release Low Molecular Weight Sulfated saccharide or sulfated oligosaccharide. Neutralization of the hydrochloric acid is accomplished by treatment with triethylamine and subsequent washing of the precipitated polyanhydride polymer with water removes the triethylamine hydrochloride byproduct. This reaction will lead to the formation of Low Molecular Weight Sulfated saccharides (molecular weight<5000. Dalton) analogs or oligosaccharides–acrylic acid co-polymer+triethylamine. Upon in vivo hydrolysis, the Low Molecular Weight Sulfated saccharides analogs will be released over time that can be controlled plus acrylic acid ethylene Co-polymer. Additionally, various PEG polymers with different branched arms (FIG. 37) are utilized for the preparation of conjugated sulfated saccharide or sulfated oligosaccharide.

Figure 37:
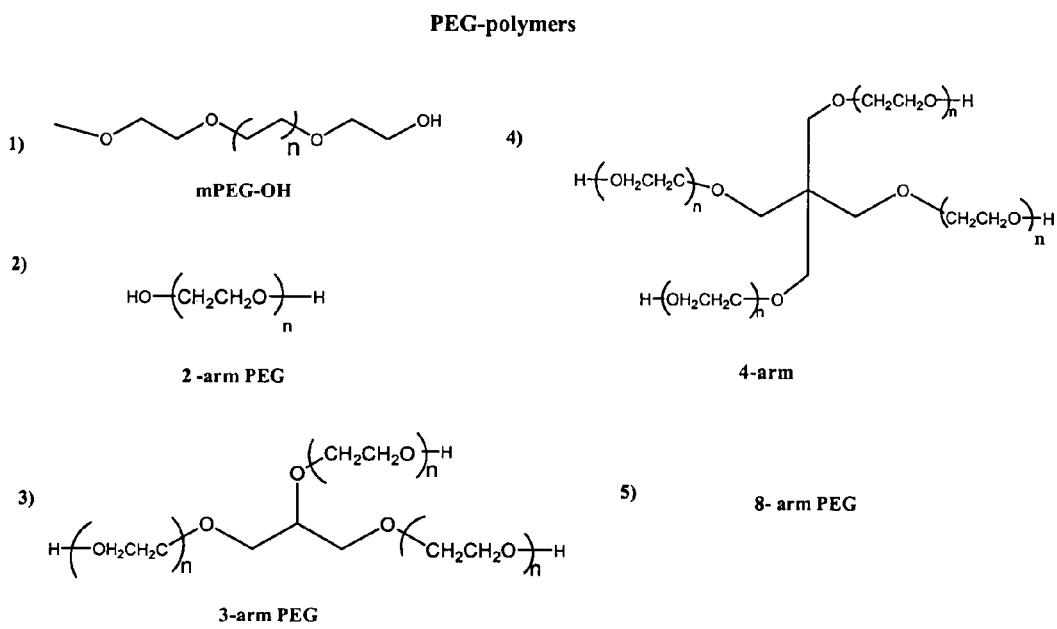
FIG. 37 depicts polyethylene glycols with different arms for different levels of loading of the sulfated saccharide or sulfated oligosaccharides, in accordance with embodiments of the present invention.

FIG. 37 depicts polyethylene glycols with different arms (1-8) for different levels of loading of the sulfated saccharide or the sulfated oligosaccharides.

Figure 38:
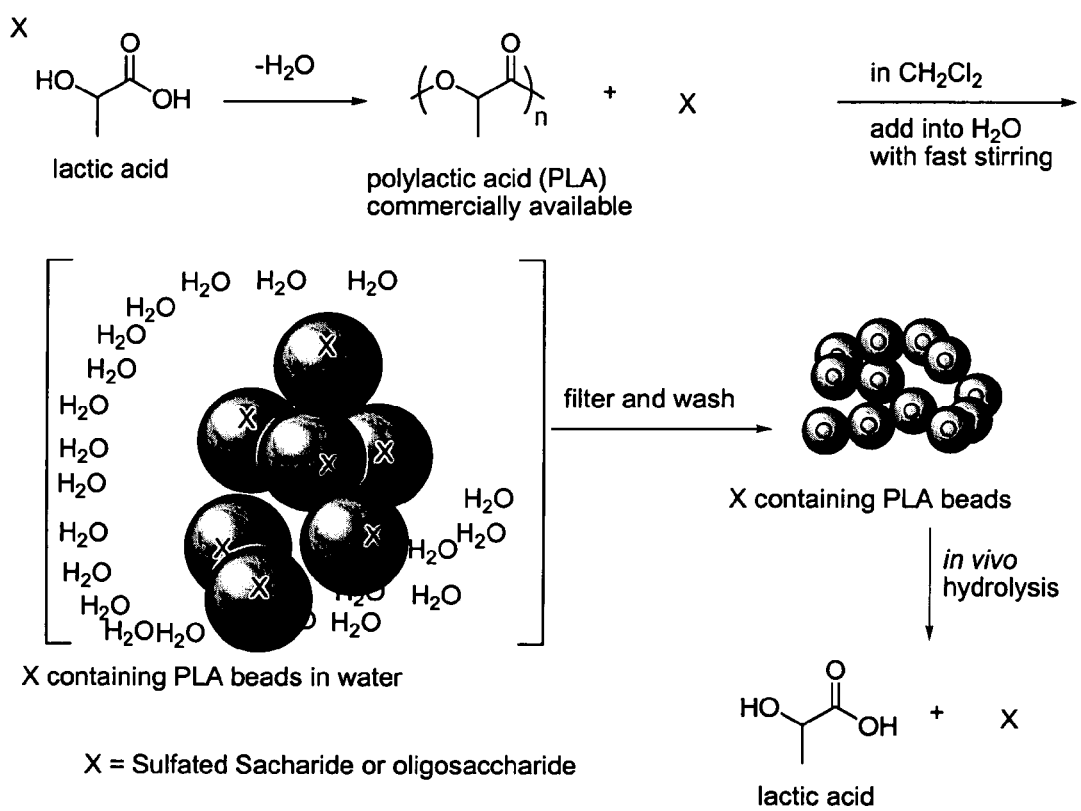
FIG. 38 depicts entrapment of sulfated saccharide/oligosaccharide in a poly-lactic acid polymer, in accordance with embodiments of the present invention.

FIG. 38 depicts entrapment of sulfated saccharide/sulfated oligosaccharide in a poly-lactic acid polymer. Poly-lactic acid polyester polymers (PLA) undergoes hydrolysis in vivo to the lactic acid monomer. The 3-nicotinic acid is linked by a chemical bond to the lactic acid polymer. As shown, the PLA polymer beads encapsulate the sulfated saccharide/sulfated oligosaccharide such that the sulfated saccharide/oligosaccharide is non-covalently conjugated to the PLA polymer beads.

Poly-lactic acid polyester polymers (PLA) undergo hydrolysis in vivo to the lactic acid monomer and this has been exploited as a vehicle for drug delivery systems in humans. Unlike the prior two covalent methods where the Low Molecular Weight Sulfated saccharides (molecular weight<5000 Dalton) analog is linked by a chemical bond to the polymer, this would be a non-covalent method that would encapsulate the Low Molecular Weight Sulfated saccharides analogs into PLA polymer beads. This reaction will lead to the formation of Low Molecular Weight Sulfated saccharides analogs or Oligosaccharides containing PLA beads in water. Filter and washing will result in the formation of Low Molecular Weight Sulfated saccharides analogs containing PLA beads, which upon in vivo hydrolysis will lead to the generation of controlled levels of Low Molecular Weight Sulfated saccharides analogs or Oligosaccharides plus lactic acid.

Figure 39:
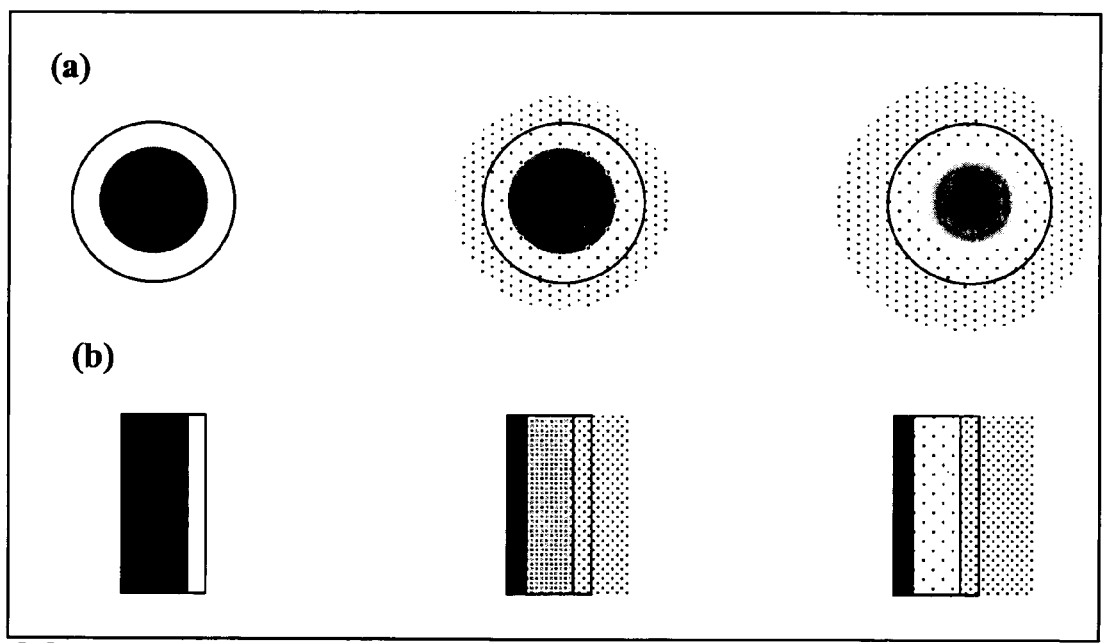
FIG. 39 depicts delivery of sulfated saccharide or oligosaccharide from typical reservoir devices, namely: (a) nano-

FIG. 39 depicts a diagrammatic sketch for the delivery of sulfated saccharide or sulfated oligosaccharide from reservoir devices, namely: (a) nano-capsule or nano-particle and (b) transdermal systems.

Disclosed herein are pro-angiogenesis agents comprising of Low Molecular Weight Sulfated saccharides or sulfated oligosaccharides (molecular weight<5000 Dalton) thereof, and polymer conjugates. The disclosed compositions can be used for promoting angiogenesis to treat disorders wherein angiogenesis is beneficial. As used herein, the term "angiogenic agent" includes any compound or substance that promotes or encourages angiogenesis, whether alone or in combination with another substance. Examples of Low Molecular Weight Sulfated saccharides (molecular weight<5000 Dalton) analogs or Oligosaccharides include, but are not limited to compositions shown in description supra of Polymer Conjugation (A), (B), and (C).

Polymer conjugations are used to improve drug delivery. While many old and new therapeutics are well-tolerated, many compounds need advanced drug discovery technologies to decrease toxicity, increase circulatory time, or modify bio-distribution. One strategy for improving drug viability is the utilization of water-soluble polymers. Various water-soluble polymers have been shown to modify bio-distribution, improve the mode of cellular uptake, change the permeability through physiological barriers, and modify the rate of clearance through the body. To achieve either a targeting or sustained-release effect, water-soluble polymers have been synthesized that contain drug moieties as terminal groups, as part of the backbone, or as pendent groups on the polymer chain.

Representative compositions of the present invention include Low Molecular Weight Glycosamino glycans, analogs thereof conjugated to polymers. Conjugation with polymers can be either through covalent or non-covalent linkages. The polymer conjugation through a covalent linkage can occur through an ester linkage (denoted as Polymer Conjugation (A)) or an anhydride linkage (denoted as Polymer Conjugation (B)). The polymer conjugation through a non-covalent linkage is denoted as Polymer Conjugation (C).

An example of a polymer conjugation through an ester linkage using polyvinyl alcohol is shown in Polymer Conjugation (A). In this preparation commercially available polyvinyl alcohol (or related co-polymers) can be esterified by treatment with the acid chloride of Low Molecular Weight Sulfated saccharides (molecular weight<5000 Dalton) analogs, including the acid chloride form. The hydrochloride salt is neutralized by the addition of triethylamine to afford triethylamine hydrochloride which can be washed away with water upon precipitation of the Low Molecular Weight Sulfated saccharides (molecular weight<5000 Dalton) analogs ester polymer form for different analogs. The ester linkage to the polymer may undergo hydrolysis in vivo to release the active pro-angiogenesis analogs (molecular weight<5000 Dalton).

An example of a polymer conjugation through an anhydride linkage using acrylic acid ethylene co-polymer as described in Polymer Conjugation (B). This is similar to the previous polymer covalent conjugation of Polymer Conjugation (A), however, this time it is through an anhydride linkage that is derived from reaction of an acrylic acid co-polymer. This anhydride linkage is also susceptible to hydrolysis in vivo to release Low Molecular Weight Sulfated saccharides analogs (molecular weight<5000 Dalton). Neutralization of the hydrochloric acid is accomplished by treatment with triethylamine and subsequent washing of the precipitated polyanhydride polymer with water removes the triethylamine hydrochloride byproduct. This reaction will lead to the formation of Low Molecular Weight Sulfated saccharides (Molecular Weight<5000 Dalton) analogs-acrylic acid co-polymer+triethylamine. Upon in vivo hydrolysis, the Low Molecular Weight Sulfated saccharides (molecular weight<5000 Dalton) analogs will be released over time that can be controlled plus acrylic acid ethylene Co-polymer.

Another representative polymer conjugation includes Low Molecular Weight Sulfated saccharides (molecular weight<5000 Dalton) analogs conjugated to polyethylene glycol (PEG). Attachment of PEG to various drugs, proteins and liposome has been shown to improve residence time and decrease toxicity. PEG can be coupled to active agents through the hydroxyl groups at the ends of the chains and via other chemical methods. PEG itself, however, is limited to two active agents per molecule. In a different approach, copolymers of PEG and amino acids were explored as novel biomaterials which would retain the biocompatibility properties of PEG, but which would have the added advantage of numerous attachment points per molecule and which could be synthetically designed to suit a variety of applications.

Another representative polymer conjugation includes Low Molecular Weight Sulfated saccharides (molecular weight<5000 Dalton) analogs in non-covalent conjugation with polymers as described in Polymer Conjugation (C). A preferred non-covalent conjugation is entrapment of Low Molecular Weight Sulfated saccharides (molecular weight<5000 Dalton) analogs thereof in a poly-lactic acid polymer. Poly-lactic acid polyester polymers (PLA) undergo hydrolysis in vivo to the lactic acid monomer and this has been exploited as a vehicle for drug delivery systems in humans. Unlike the prior two covalent methods where the Low Molecular Weight Sulfated saccharides analogs is linked by a chemical bond to the polymer, this would be a non-covalent method that would encapsulate the Low Molecular Weight Sulfated saccharides analogs peptide or analogs into PLA polymer beads. This reaction will lead to the formation of Low Molecular Weight Sulfated saccharides analogs containing PLA beads in water. Filter and washing will result in the formation of Low Molecular Weight Sulfated saccharides analogs containing PLA beads, which upon in vivo hydrolysis will lead to the generation of controlled levels of Low Molecular Weight Sulfated saccharides analogs plus lactic acid.

Furthermore, nanotechnology can be used for the creation of useful materials and structures sized at the nanometer scale. The main drawback with biologically active substances is fragility. Nano-scale materials can be combined with such biologically active substances to dramatically improve the durability of the substance, create localized high concentrations of the substance and reduce costs by minimizing losses. Therefore, additional polymeric conjugations include nano-particle formulations of Low Molecular Weight Sulfated saccharides analogs thereof. In such an embodiment, nano-particles (e.g., nano-polymers) can be used as a matrix for local delivery of analogs. This will aid in time controlled delivery into the cellular and tissue target.

Compositions of the present invention include Low Molecular Weight Glycosamino glycans, and derivatives either alone or in covalent or non-covalent conjugation with polymers.

As provided above, methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of Low Molecular Weight Sulfated saccharides (molecular weight<5000 Dalton) or analogs, polymeric forms, and derivatives. The methods involve the co-administration of an effective amount of Low Molecular Weight Sulfated saccharides analogs, polymeric forms, and derivatives in low, daily dosages for a week or more with other standard pro-angiogenesis growth factors, vasodilators, anticoagulants, thrombolytics or other vascular-related therapies.

EXAMPLES

Standard experimental methods were used to study the effects of saccharides and oligosaccharides and on endothelial cell tube assembly and new blood vessel formation, as described in the following examples.

Example 1

Materials

All reagents were chemical grade and purchased from Sigma Chemical Co. (St. Louis, Mo.) or through VWR Scientific (Bridgeport, N.J.). Cortisone acetate, bovine serum albumin (BSA), and gelatin solution (2% type B from bovine skin) were purchased from Sigma Chemical Co. (St. Louis, Mo.). M199 growth medium with Earl's salts, basic FGF, Insulin-Transferrin-Selenium-G Supplement (I-T-Se) 100×, Dulbecco's phosphate buffered salt solution (PBS) with and without $Ca^{+2}$ and $Mg^{+2}$, and 0.5 M EDTA were obtained from Gibco BRL (Grand Island, N.Y.). Human umbilical vein endothelial cells (HUVEC), endothelial cell basal medium (serum-free, EBM), endothelial growth medium (EGM) (supplemented with growth factors, fetal calf serum), and 0.025% trypsin/0.01% EDTA solution were purchased from Clonetics Inc. (San Diego, Calif.). Human prostrate (TSU-Pr) tumor cells were obtained from American Type Culture Collection (Rockville, Md.). Matrigel® matrix and human collagen type III were purchased from Becton Dickinson (Bedford, Mass.). HEMA-3 fixative and staining solutions were purchased from Biochemical Sciences, Inc. (Swedesboro, N.J.). Fertilized chicken eggs were purchased from Charles River Laboratories, SPAFAS Avian Products & Services (North Franklin, Conn.).

Example 2

In Vitro 3D Sprout Angiogenesis of Human Micro-Vascular Endothelial Cells

Culture of HDMEC on micro-carrier beads: 80% confluent HDMEC (Passage 5-10) were mixed with gelatin-coated Cytodex-3 beads with a ratio of 40 cells per bead. Cells and beads (150-200 beads per well for 24-well plate) are suspended with 5 ml EBM+15% normal human serum. The suspension is mixed gently every one hour for first four hours The mixture culture is left in a $CO_2$ incubator overnight. The next morning, 10 ml of fresh EBM+15% HS is added and the mixture culture is cultured for another three hours. Before experiments, the culture of EC-beads is checked. 500 μl of PBS are added in a well of 24-well plate. 100 ul of the EC-bead culture solution is removed added to the PBS. The number of beads is counted and the concentration of EC-beads is calculated. The EC-beads are good for experiments for 48 hours.

Fibrinogen solution (1 mg/ml) in EBM medium is prepared with or without angiogenesis factors or testing factors. For positive control, 30 ng/ml VEGF+25 ng/ml FGF2 is used. EC-beads are with EBM medium for two times and added to fibrinogen solution. For each condition, experiments are performed in triplicates. The EC-beads are mixed in fibrinogen solution gently. 2.5 μl human thrombin (0.05 U/μl) are added in 1 ml fibrinogen solution 300 ul is immediately transferred to each well of 24-well plate. The fibrinogen solution will polymerize in 5-10 minutes. After 20 minutes, EBM+20% normal human serum+10 ug/ml Aprotinin is added. Next, the plate is incubated in $CO_2$ incubator. It takes about 24-48 hrs for HDMEC to invade fibrin gel and form tubes. Human dermal micro-vascular endothelial cells (HDMVC) passage 11 was used. Images were taken at 4 and 10×, day 6. Cells were pretreated with FGF (2.5 ng)+VEGF (5 ng).

Example 3

Neovascularization in the Chick Chorioallantoic Membrane (CAM) and Microscopic Analysis of CAM Sections In vivo neovascularization was examined by the method previously described by Auerbach et al. (Auerbach et al., *J. Dev. Biol.*, 41:391-394 (1974), which is hereby incorporated by reference in its entirety). Ten-day old embryos were purchased from Spafas, Inc. (Preston, Conn.) and were incubated at 37° C. with 55% relative humidity. In the dark with the help of a candling lamp, a small hole was punctured in the shell concealing the air sac with a hypodermic needle. A second hole was punctured in the shell on the broadside of the egg directly over an avascular portion of the embryonic membrane, as observed during candling. A false air sac was created beneath the second hole by the application of negative pressure to the first hole, which caused the chorioallantoic membrane (CAM) to separate from the shell. A window, approximately 1.0 $cm^2$, was cut in the shell over the dropped CAM with the use of a small crafts grinding wheel (Dremel, Division of Emerson Electric Company Racine, Wis.) which allowed direct access to the underlying CAM. Filter disks of #1 filter paper (Whatman International, United Kingdom) were soaked in 3 mg/ml cortisone acetate (Sigma, St. Louis, Mo.) in a solution of 95% ethanol and water and subsequently air dried under sterile conditions. FGF2 (Life Technologies, Gaithersburg, Md.) was used to grow vessels on the CAMs of 10 day old chick embryos. Sterile filter disks adsorbed with FGF2 dissolved in PBS at 1 µg/ml were placed on growing CAMs. Sterile filter disks adsorbed with FGF2 or PAR2 activating agonists were dissolved in PBS at 1 µg/ml were placed on growing CAM. At 24 h, test compounds or control vehicle was added directly to CAM topically.

CAM tissue directly beneath FGF2-saturated filter disk was resected from embryos treated 48 hours prior with test compound or control. Tissues were washed three times with PBS. Sections were placed in a 35-mm petri dish (Nalge Nunc, Rochester, N.Y.) and examined under a SV6 stereomicroscope (Karl Zeiss, Thornwood, N.Y.) at 50× magnification. Digital images of CAM sections adjacent to filters were collected using a 3-CCD color video camera system (Toshiba America, New York, N.Y.) and analyzed using Image-Pro Plus software (Media Cybernetics, Silver Spring, Md.).

CAM tissue directly beneath FGF2-saturated filter disk was resected from embryos treated 48 h prior with compound or control. Tissues were washed three times with PBS. Sections were placed in a 35-mm petri dish (Nalge Nunc, Rochester, N.Y.) and examined under a SV6 stereomicroscope (Karl Zeiss, Thornwood, N.Y.) at 50× magnification. Digital images of CAM sections adjacent to filters were collected using a 3-CCD color video camera system (Toshiba America, New York, N.Y.) and analyzed with the Image-Pro Plus software (Media Cybernetics, Silver Spring, Md.).

Example 4

The Effect of Low Molecular Weight Sulfated Saccharides (Molecular Weight<5000 Dalton) Over Time on Human Endothelial Cell Sprouting in 3 D Fibrin Beads Growth factors: VEGF (30 ng/ml)+FGF2 (25 ng/ml) CH2: Sulfated Hexasaccharide at 10 ug/ml. While in vivo assays, such as the CAM assay, are routinely used in evaluating angiogenesis, in vitro assays can offer a convenient alternative. A quantitative three-dimensional in vitro assay method was utilized to screen compounds for angiogenic activity. Gelatin-coated beads were used to support endothelial cells in a fibrin gel matrix (FIG. 22).

FIG. 22 depicts in vitro angiogenesis assay of structurally defined, homogenous heparin-derived oligosaccharides in the presence of VEGF and b-FGF. Portions A-F of FIG. 22 are as follows: (A) Oligosaccharide structure; (B) Beads with disaccharide (dp 2); (C) Beads with tetrasaccharide (dp 4); (D) Beads with hexasaccharide (dp 6); (E) Beads with octasaccharide (dp 8); (F) Beads with decasaccharide (dp 10). Qualification of CAM data for the same oligosaccharide afforded 115±6, 135±9, 160±11, 161±8, 165±12 near branch points for oligosaccharides dp 2, dp 4, dp 6, and dp 8, respectively. Data from the CAM assay represent mean±SD, n=8 per group.

The cells on the gelatin-coated beads were treated with sub-threshold levels of VEGF (1.25 ng/ml) and b-FGF (2.5 ng/ml) in the presence and absence of agent to be tested; angiogenesis response was recorded by video image capture, and capillary sprouts were counted. No significant sprouting was demonstrated at the sub-threshold levels of VEGF (1.25 ng/ml) plus b-FGF (2.5 ng/ml).

Heparin oligosaccharides of defined structure and size were prepared. These linear oligosaccharides have a charge density of −2/saccharide unit (3 sulfo groups and 1 carboxyl group per disaccharide repeating unit). Oligosaccharides ranging from disaccharide (dp 2) to decasaccharides (dp 10) were examined using the three-dimensional in vitro assay at a concentration of 10 ug/ml (FIG. 22). These defined heparin oligosaccharides exhibited pro-angiogenic activity that clearly increased with chain size. The in vivo CAM assay gave identical results, showing an increase in angiogenic effect from disaccharide (dp 2) to hexasaccharide (dp 6) with no significant differences observed from hexasaccharide (dp 6) to decasaccharide (dp 10).

Example 5

Pro-Angiogenesis Activity of Linear Synthetic Oligosaccharides

Figure 23:
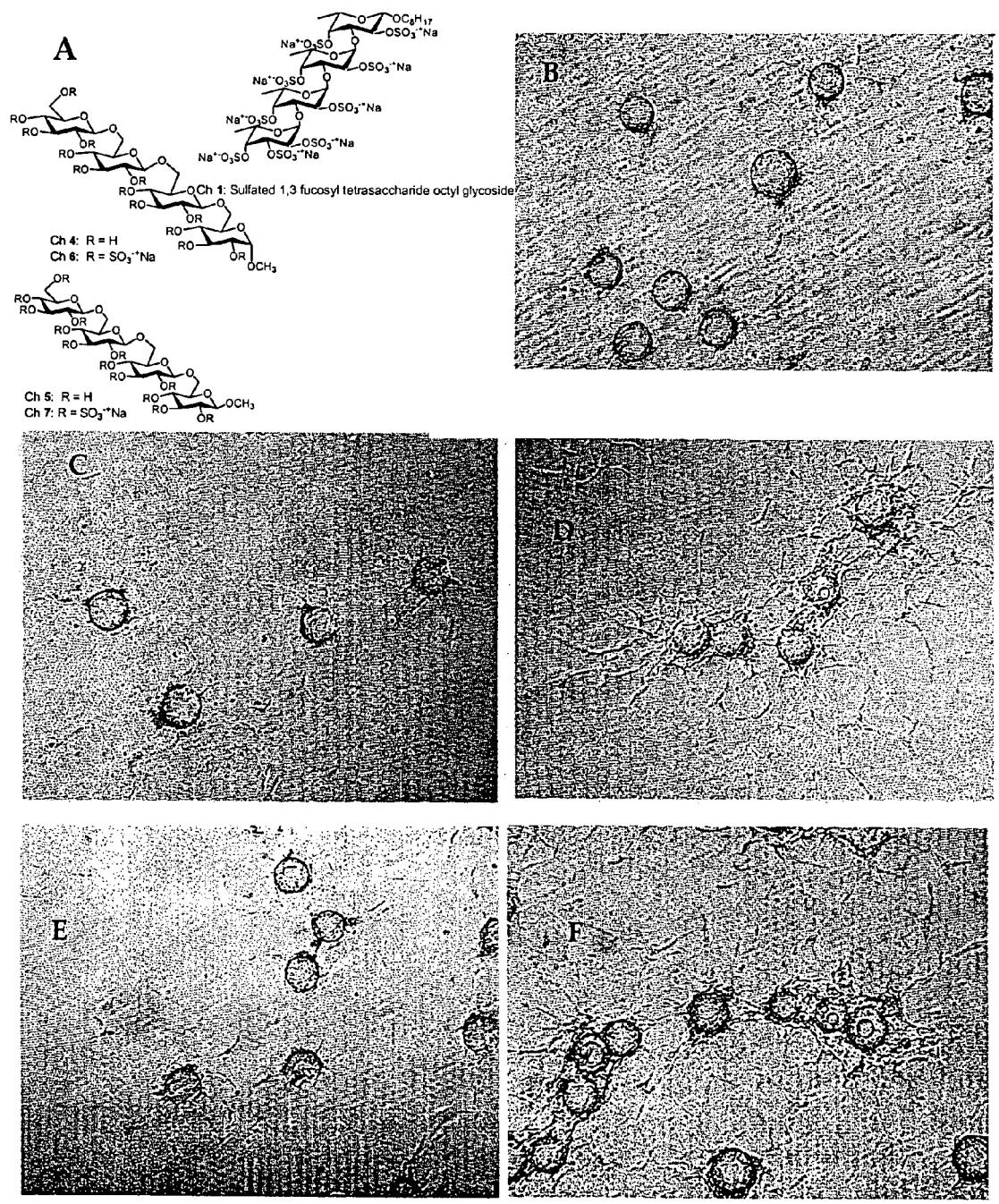
FIG. 23 depicts the evaluation of linear synthetic oligosaccharides using three-dimensional in vitro angiogenesis assay in the presence of sub-threshold concentration of VEGF and b-FGF, in accordance with embodiments of the present invention.

The in vitro angiogenic activity of synthetically prepared analogs of heparin oligosaccharides were examined, starting with linear tetrasaccharides, comprised of various saccharide units and having a charge density of 0 to −3/saccharide unit (FIG. 23).

FIG. 23 depicts the evaluation of linear synthetic oligosaccharides using three-dimensional in vitro angiogenesis assay in the presence of sub-threshold concentration of VEGF (1.25 ng/ml) and b-FGF (2.5 ng/ml). Portions A-F of FIG. 23 are as follows: (A) structure of Ch 1, Ch 4, Ch 5, Ch 6, and Ch 7;

(B-F) pro-angiogenesis activity of Ch 1, Ch 4, Ch 5, Ch 6, and Ch 7 in the three-dimensional HMDEC sprouting assay.

A linear fucose tetrasaccharide (Ch 1), with a charge density of −2/saccharide unit, showed no angiogenic activity. Two-linear glucose tetrasaccharides (Ch 6 and Ch 7) with a charge density of −3/saccharide unit showed potent pro-angiogenic activity, while their un-sulfated counterparts (Ch 4 and Ch 5 with a charge density of 0/saccharide unit) showed only slight pro-angiogenic activity. A linear xylose hexasaccharide (Ch 3) having a charge density of −1/saccharide unit showed no angiogenic activity (FIG. 24).

FIG. 24 depicts a comparison of branched versus linear sulfated synthetic oligosaccharides three-dimensional in vivo angiogenesis assay in the presence of VEGF and b-FGF. Portions A-E of FIG. 24 are as follows: (A) Ch 2 (top structure-branched) versus Ch3 (bottom structure-linear) sulfated synthetic oligosaccharides; (B) Control with VEGF and b-FGF but no added oligosaccharide; (C) Ch 2 activity; (D) Ch 3 activity; (E) graph showing the increase in tube length with the sulfated hexasaccharides Ch 2 versus Ch 3 as compared to control.

Example 6

Angiogenic Activity of Branched Synthetic Oligosaccharides

A doubly branched glucose hexasaccharide (Ch 2, having a charge density of −3/saccharide unit) showed highly potent pro-angiogenic activity in the three-dimensional in vitro assay (FIG. 24). A linear hexasaccharide (Ch 3, having a charge density of −1/saccharide unit) showed no angiogenic activity. The doubly branched, un-sulfated hexasaccharide analog of Ch 2 and Ch 8 showed substantially reduced pro-angiogenic activity as compared to their respective corresponding sulfated saccharides, Ch 10 and Ch 9 (Table 2). Singly branched glucose trisaccharides, Ch 8 and Ch 9, containing the three saccharides closest to the reducing end of Ch 1 and 10, represent a simplification of these studies. The singly branched sulfated trisaccharide Ch 9 showed diminished pro-angiogenic activity compared with Ch 1, and the singly branched un-sulfated trisaccharide Ch 8 showed diminished pro-angiogenic activity compared with Ch 10 (data not shown).

TABLE 2

Effect of Sulfation on the Pro-angiogenesis Efficacy of Saccharides in the Chorioallantoic Membrane Model

| Treatment | Mean Branch Points ± SEM |
| --- | --- |
| PBS (control) | 78 ± 9 |
| Ch 10 (10 µg) | 123 ± 10 |
| Ch 2 (10 µg) | 177 ± 11* |
| Ch 8 (10 µg) | 115 ± 6 |
| Ch 9 (10 µg) | 162 ± 7* |

Data represent mean ± SEM,
n = 8 per group;
*P < 0.01.
Ch 10 and Ch 8 are the non-sulfated saccharides corresponding to the sulfated saccharides Ch 2 and Ch 9.

Example 7

Angiogenic Properties of Potent, Branched, Sulfated, Synthetic Oligosaccharide

Figure 25:
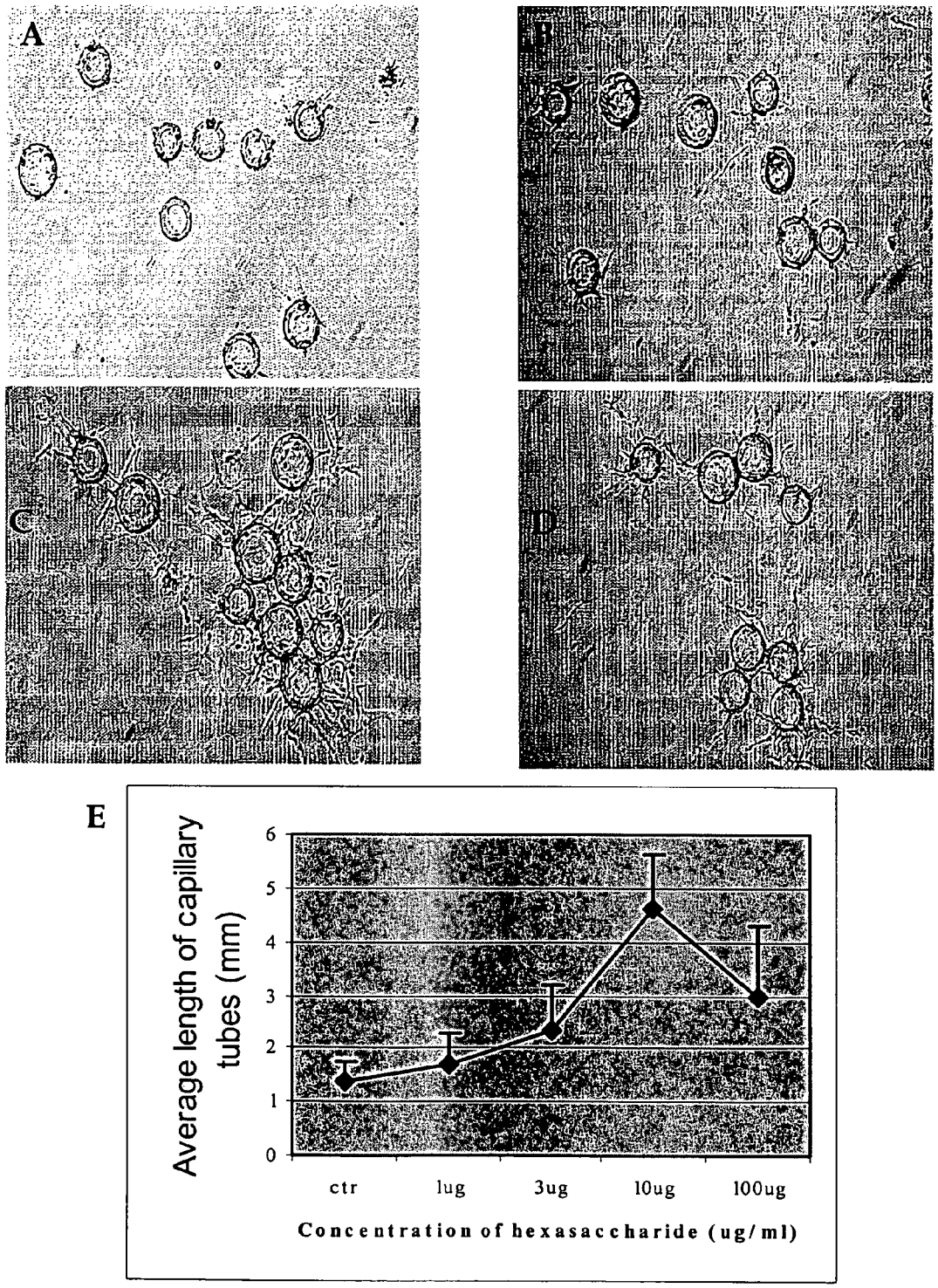
FIG. 25 depicts dose response of the pro-angiogenic activity of Ch 2 measured using the three-dimensional in vitro assay in the presence of VEGF and b-FGF at day 7, in accordance with embodiments of the present invention.

FIG. 25 depicts dose response of the pro-angiogenic activity of Ch 2 measured using the three-dimensional in vitro assay in the presence of VEGF and b-FGF at day 7. Portions A-E of FIG. 25 are as follows: (A) activity at 0 µg/ml; (B) activity at 1 µg/ml; (C) activity at 10 µg/ml; (D) activity at 100 µg/ml; (E) graph demonstrating the dose-dependent effect on the pro-angiogenesis efficacy of the saccharides versus VEGF plus b-FGF (control) in the three-dimensional angiogenesis sprouting assay.

Figure 26:
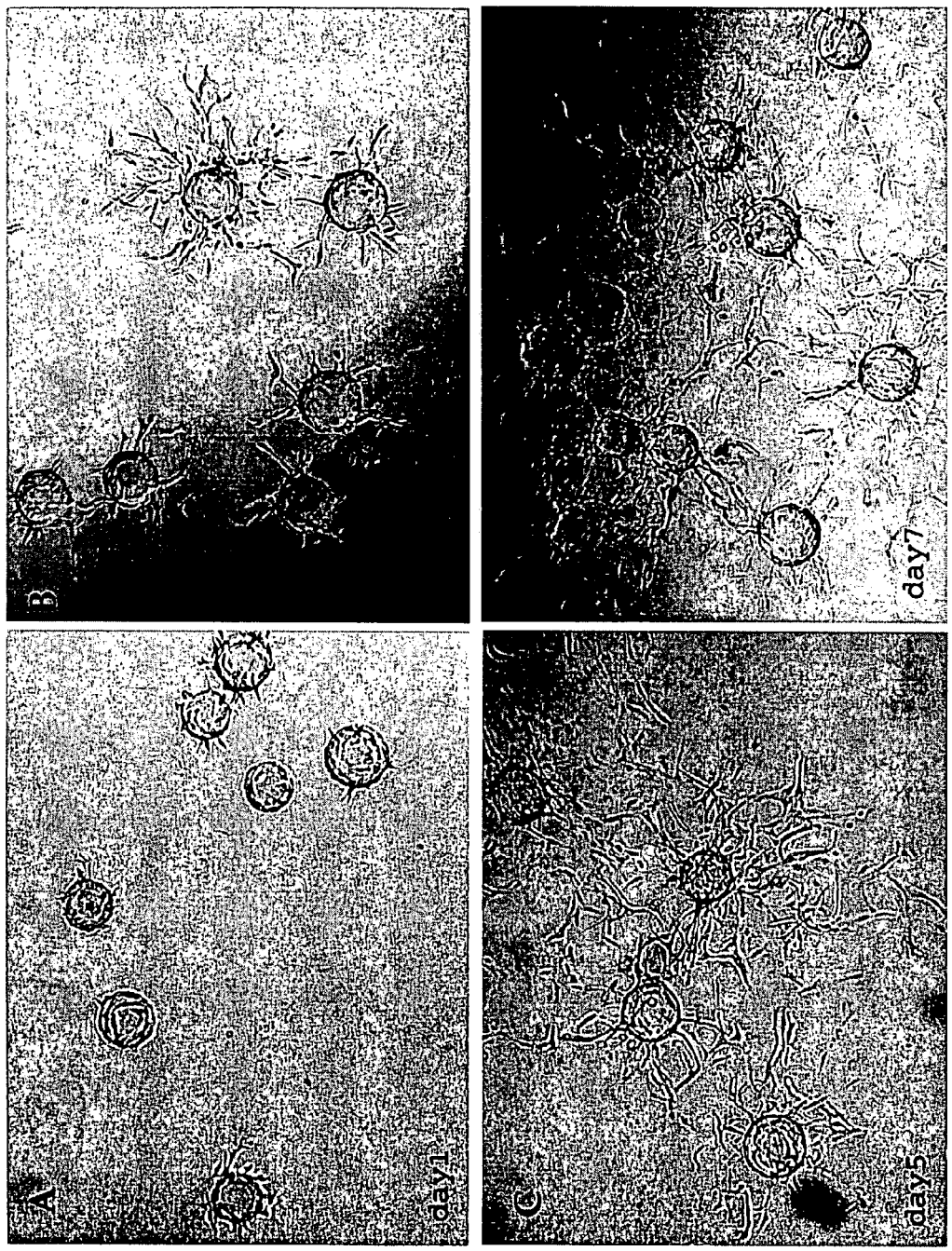
FIG. 26 depicts time-dependent pro-angiogenic effect of Ch 2 using the three-dimensional in vitro assay in the presence of VEGF and b-FGF, in accordance with embodiments of the present invention.

FIG. 26 depicts time-dependent pro-angiogenic effect of Ch 2 using the three-dimensional in vitro assay in the presence of VEGF and b-FGF. Portions A-D of FIG. 26 are as follows: (A) activity at day 1; (B) Activity at day 3; (C) Activity at day 5; (D) Activity at day 7.

Figure 27:
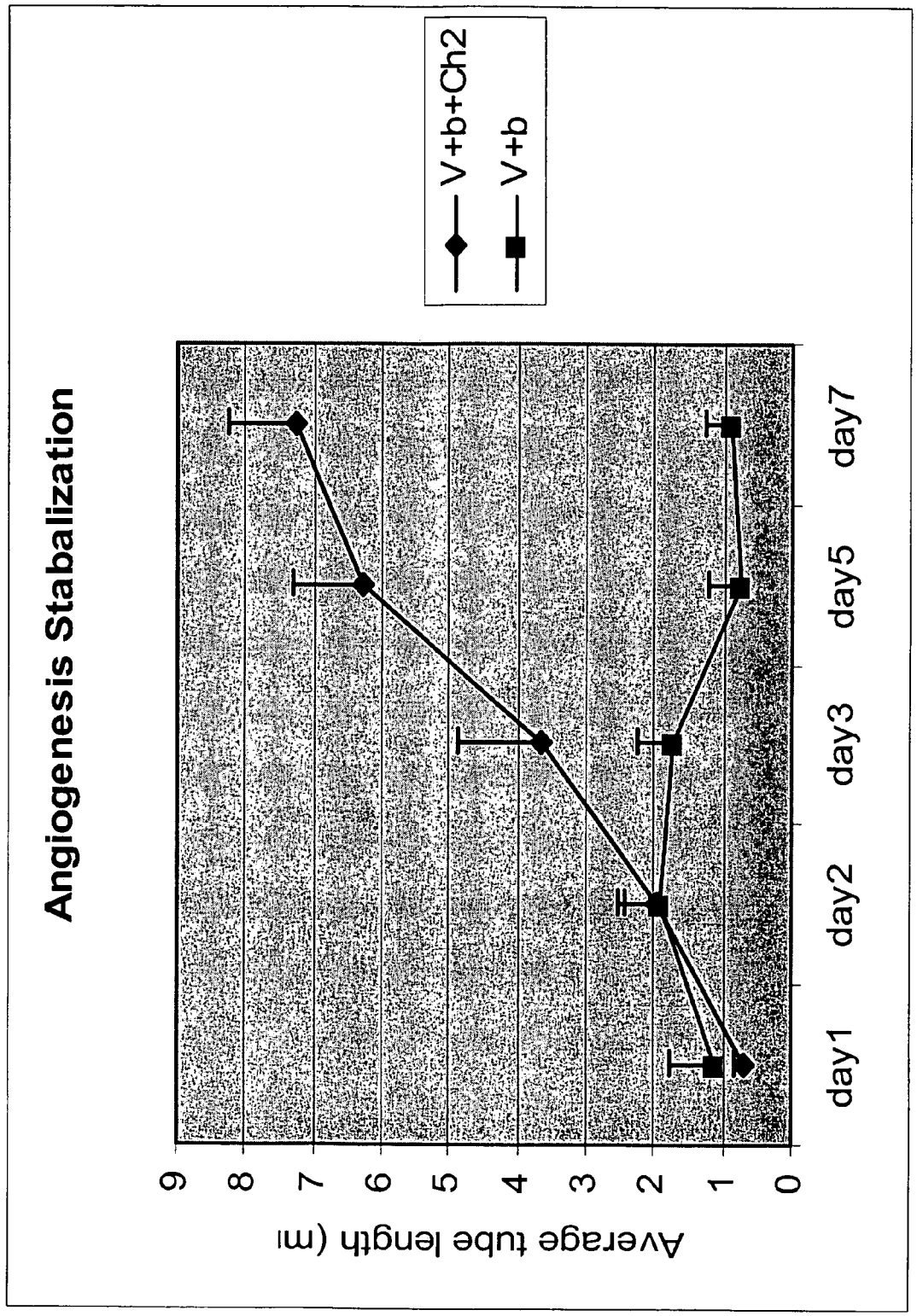
FIG. 27 depicts a graph representing the average tube length measured using the three-dimensional in vitro assay as a function of time, in accordance with embodiments of the present invention.

FIG. 27 depicts a graph representing the average tube length measured using the three-dimensional in vitro assay as a function of time. The symbol (■) denotes VEGF and b-FGF control. The symbol (♦) denotes VEGF, b-FGF and Ch 2.

FIG. 28 depicts effect of heparin oligosaccharide chain length on pro-angiogenesis in the in vivo CAM model. Mean±SD are show for the data; n=8 per group.

FIG. 29 depicts representative illustration for the pro-angiogenesis effect of sulfated saccharide analogs versus b-FGF or VEGF in the CAM model. Control CAMs (n=8/group/experiment) were exposed to PBS (vehicle, control) and sulfated saccharide analogs at 1-10 ug or 1.0 ug b-FGF for 3 days. Sulfated saccharide analogs, VEGF, or b-FGF resulted in maximal increase in blood vessel branching, as shown in these representative images.

The results shown in FIGS. 24-30 are as follows. The most active pro-angiogenic oligosaccharide (Ch 2) was evaluated at a variety of concentrations (FIGS. 24 and 25). A dose response curve was obtained, with peak activity observed at a concentration of 10 µg/ml (FIG. 25). A 10-fold increase in concentration to 100 µg/ml showed no significant change in activity in the three-dimensional in vitro assay. Using the optimum dose of 10 µg/ml, the time dependence of the pro-angiogenic activity of Ch 2 was next examined (FIG. 26). A maximum effect in the three-dimensional in vitro assay was observed between day 5 and day 7. Moreover, in the absence of Ch 2, a maximum pro-angiogenic effect for VEGF (25 ng/ml) and b-FGF (30 ng/ml) alone, observed at day 2, was similar to that observed for VEGF and b-FGF in the presence of 10 µg/ml of Ch 2 (FIG. 27). While the activity of maximal concentrations of VEGF (25 ng/ml) and b-FGF (30 ng/ml) alone declined after day 2, the activity of VEGF and b-FGF in the presence of 10 µl/ml of Ch 2 continued to increase, reaching a maximum between day 5 and day 7. Data demonstrated that the globular sulfated hexasaccharide (Ch 2) promoted angiogenesis and sustained the survival of the new vessels while VEGF and FGF2 initiated the vessels but did not sustain it. Saccharides differentially regulate new blood vessel with optimal potency with globular sulfated hexasaccharide (Ch 2).

The results obtained in the in vivo CAM assay further confirmed this observation with Ch2 (FIG. 28). Additionally, the effect of chain length on the pro-angiogenesis efficacy was demonstrated in the CAM assay, with a maximal increase in new vessel branch points with the hexasaccharide (FIG. 28, 29).

Example 8

Mechanistic Evaluation of Pro-Angiogenic Effect of Potent Oligosaccharide

Initial studies on the mechanism of action of Ch 2 were next undertaken. The role of the ERK1/2 in the signal transduction pathway in stimulation of angiogenesis by Ch 2 was first assessed. Studies on ERK1/2 inhibition were carried out in the three-dimensional in vitro micro-vascular sprouting assay. Oligosaccharide Ch 2 at 10 μg caused a significant increase in tube length and number of migrating cells, an effect that was blocked by PD 98059 (P<0.01) (Table 2). Next, the role of the integrin αvβ3 in the stimulation of angiogenesis by Ch 2 was studied. Angiogenesis promoted by Ch 2 (10 μg) in the presence of sub-threshold levels of VEGF and b-FGF was significantly (P<0.01) blocked by the αvβ3 integrin antagonist XT199 (Table 3). Similar results were shown when using the αvβ3 antibody, LM609 (data not shown). These data suggest that the pro-angiogenesis effects of sulfated saccharides begin at the plasma membrane αvβ3 integrin and involve activation of the ERK1/2.

TABLE 3

Effect of MAP Kinase (ERK1/2) Inhibitor (PD9805) or αvβ3 Integrin Antagonist (XT199) on the Pro-angiogenesis Efficacy of Branched Sulfated Hexasaccharide in Ch 2 the Chorioallantoic Membrane Model

| Treatment Groups | Mean Branch Points ± SEM | Mean % Inhibition ± SEM |
|---|---|---|
| PBS (control) | 76 ± 7 | |
| PBS + Ch 2 (10 μg) | 153 ± 3 | |
| PBS + Ch 2 (10 μg) + PD9805 (4.8 μg) | 95 ± 8 | 71 ± 6* |
| PBS + Ch 2 (10 μg) + XT199 (4.8 μg) | 103 ± 6 | 67 ± 5* |

Data represent mean ± SEM,
n = 8 per group;
*P < 0.01.
PD9805 is a MAP (ERK1/2) inhibitor and
XT199 is a potent and specific αvβ3 integrin antagonist.

Example 9

In Vitro Human Epithelial and Fibroblast Wound Healing

The in vitro 2-dimensional wound healing method is as described in Mohamed S, Nadijcka D, Hanson, V. Wound healing properties of cimetidine in vitro. Drug Intell Clin Pharm 20: 973-975; 1986, incorporated herein by reference in its entirety. Additionally, a 3-dimensional wound healing method already established in our Laboratory will be utilized in this study (see below). Data show potent stimulation of wound healing by Low Molecular Weight Sulfated saccharides.

In Vitro 3D Wound Healing Assay of Human Dermal Fibroblast Cells:

Step 1: Prepare Contracted Collagen Gels:
  1) Coat 24-well plate with 350 ul 2% BSA at RT for 2 hr,
  2) 80% confluent NHDF (normal human dermal fibroblast cells, Passage 5-9) are trypsinized and neutralized with growth medium, centrifuge and wash once with PBS
  3) Prepare collagen-cell mixture, mix gently and always on ice:

| Stock solution | Final Concentration |
|---|---|
| 5 × DMEC | 1 × DMEM |
| 3 mg/ml vitrogen | 2 mg/ml |
| ddH2O | optimal |
| NHDF | 2 × 10~5 cells/ml |
| FBS | 1% |

4) Aspire 2% BSA from 24 well plate, add collagen-cell mixture 350 ul/well, and incubate the plate in 37° C. CO2 incubator.
  5) After 1 hr, add DMEM+5% FBS medium 0.5 ml/well, use a 10 ul tip Detach the collagen gel from the edge of each well, then incubate for 2 days. The fibroblast cells will contract the collagen gel Step 2: Prepare 3D Fibrin Wound Clot and Embed Wounded Collagen Culture
  1) Prepare fibrinogen solution (1 mg/ml) with or without testing regents. 350 ul fibrinogen solution for each well in eppendorf tube.

| Stock solution | Final Concentration |
|---|---|
| 5 × DMEC | 1 × DMEM |
| Fibrinogen | 1 mg/ml |
| ddH2O | optimal |
| testing regent's | optimal concentration |
| FBS | 1% or 5% |

2) Cut each contracted collagen gel from middle with scissors. Wash the gel with PBS and transfer the gel to the center of each well of 24 well plate
  3) Add 1.5 ul of human thrombin (0.25 U/ul) to each tube, mix well and then add the solution around the collagen gel, the solution will polymerize in 10 minutes.

After 20 mins, add DMEM+1% (or 5%) FBS with or without testing agent, 450 ul/well and incubate the plate in 37° C. CO$_2$ incubator for up to 5 days. Take pictures on each day.

Example 10

In Vivo Wound Healing in Diabetic Rats

Using an acute incision wound model in diabetic rats, the effects of Low Molecular Weight Sulfated saccharides (molecular weight<5000 Dalton) analogs and its conjugated forms are tested. The rate of wound closure, breaking strength analyses and histology are performed periodically on days 3-21.

In part, this invention provides compositions and methods for promoting angiogenesis in a subject in need thereof. Conditions amenable to treatment by promoting angiogenesis include, for example, occlusive peripheral vascular disease and coronary diseases, in particular, the occlusion of coronary vessels, and disorders associated with the occlusion of the peripheral vasculature and/or coronary blood vessels, erectile dysfunction, stroke, and wounds. Also disclosed are compositions and methods for promoting angiogenesis and/or recruiting collateral blood vessels in a patient in need thereof. The compositions include an effective amount of polymeric forms of Low Molecular Weight Sulfated saccharides (molecular weight<5000 Dalton) analogs and derivatives and an effective amount of an adenosine and/or nitric oxide donor. The compositions can be in the form of a sterile, injectable, pharmaceutical formulation that includes an effective amount of Low Molecular Weight Sulfated saccharides analogs and adenosine derivatives in a physiologically and pharmaceutically acceptable carrier, optionally with one or more excipients.

A major reason for heart failure following acute myocardial infarction is an inadequate response of new blood vessel formation, i.e., angiogenesis. Low Molecular Weight Sulfated saccharides analogs are beneficial in heart failure and stimulate coronary angiogenesis. The methods of the invention include, in part, delivering a single treatment of a Low Molecular Weight Sulfated saccharides analogs at the time of infarction either by direct injection into the myocardium or by simulation of coronary injection by intermittent aortic ligation to produce transient isovolumic contractions to achieve angiogenesis and/or ventricular remodeling.

Accordingly, in one aspect the invention features methods for treating occlusive vascular disease, coronary disease, myocardial infarction, ischemia, stroke, and/or peripheral artery vascular disorders by promoting angiogenesis by administering to a subject in need thereof an amount of a polymeric form of Low Molecular Weight Sulfated saccharides analogs, or an analog thereof, effective for promoting angiogenesis.

Examples of polymeric forms of Low Molecular Weight Sulfated saccharides (molecular weight<5000 Dalton) analogs, conjugated to polyvinyl alcohol, acrylic acid ethylene co-polymer or poly-lactic acid are provided herein.

The methods also involve the co-administration of Low Molecular Weight Sulfated saccharides analogs and an effective amount of an adenosine and/or nitric oxide (NO) donor in low, daily dosages for a week or more. One or both components can be delivered locally via catheter. Low Molecular Weight Sulfated saccharides analogs peptides, analogs, and derivatives in vivo can be delivered to capillary beds surrounding ischemic tissue by incorporation of the compounds in an appropriately sized liposome or microparticle. Low Molecular Weight Sulfated saccharides analogs peptides, analogs, polymeric forms and derivatives can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart including, for example, occlusive peripheral vascular disease (also known as peripheral arterial occlusive disease), or erectile dysfunction.

Wound angiogenesis is an important part of the proliferative phase of healing. Healing of any skin wound other than the most superficial cannot occur without angiogenesis. Not only does any damaged vasculature need to be repaired, but the increased local cell activity necessary for healing requires an increased supply of nutrients from the bloodstream. Moreover, the endothelial cells which form the lining of the blood vessels are important in themselves as organizers and regulators of healing.

Thus, angiogenesis provides a new microcirculation to support the healing wound. The new blood vessels become clinically visible within the wound space by four days after injury. Vascular endothelial cells, fibroblasts, and smooth muscle cells all proliferate in coordination to support wound granulation. Simultaneously, re-epithelialization occurs to reestablish the epithelial cover. Epithelial cells from the wound margin or from deep hair follicles migrate across the wound and establish themselves over the granulation tissue and provisional matrix. The role of topically applied Low Molecular Weight Sulfated saccharides (molecular weight<5000 Dalton) analogs or polymeric forms in wound healing therefore represents a novel strategy to accelerate wound healing in diabetics and in non-diabetics with impaired wound healing abilities. Topical administration can be in the form of attachment to a band-aid. Additionally, nano-polymers and nano-particles can be used as a matrix for local delivery of Low Molecular Weight Sulfated saccharides analogs and its analogs. This will aid in time controlled delivery into the cellular and tissue target.

Accordingly, another embodiment of the invention features methods for treating wounds by promoting angiogenesis by administering to a subject in need thereof an amount of a polymeric form of Low Molecular Weight Sulfated saccharides analogs, or an analog thereof, effective for promoting angiogenesis.

Low Molecular Weight Sulfated saccharides analogs, polymeric forms, and derivatives can be used in a method for promoting angiogenesis in a patient in need thereof. The method involves the co-administration of an effective amount of Low Molecular Weight Sulfated saccharides analogs, polymeric forms, and derivatives in low, daily dosages for a week or more. The method may be used as a treatment to restore cardiac function after a myocardial infarction. The method may also be used to improve blood flow in patients with coronary artery disease suffering from myocardial ischemia or inadequate blood flow to areas other than the heart, for example, peripheral vascular disease, for example, peripheral arterial occlusive disease, where decreased blood flow is a problem.

The compounds can be administered via any medically acceptable means which is suitable for the compound to be administered, including oral, rectal, topical or parenteral (including subcutaneous, intramuscular and intravenous) administration. For example, adenosine has a very short half-life. For this reason, it is preferably administered intravenously. However, adenosine $A_2$ agonists have been developed which have much longer half-lives, and which can be administered through other means. Low Molecular Weight Sulfated saccharides (molecular weight<5000 Dalton) analogs, polymeric forms, and derivatives can be administered, for example, intravenously, oral, topical, intranasal administration.

In some embodiments, the Low Molecular Weight Sulfated saccharides analogs, polymeric forms, and derivatives are administered via different means. The amounts of the Low Molecular Weight Sulfated saccharides analogs peptides, its analogs, polymeric forms, and derivatives required to be effective in stimulating angiogenesis will, of course, vary with the individual being treated and is ultimately at the discretion of the physician. The factors to be considered include the condition of the patient being treated, the efficacy of the particular adenosine $A_2$ receptor agonist being used, the nature of the formulation, and the patient's body weight. Occlusion-treating dosages of Low Molecular Weight Sulfated saccharides analogs or its polymeric forms, and derivatives are any dosages that provide the desired effect.

The compounds described above are preferably administered in a formulation including Low Molecular Weight Sulfated saccharides analogs or its polymeric forms, and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing the active compound (s), which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the Low Molecular Weight Sulfated saccharides (molecular weight<5000 Dalton) analogs or its polymeric forms, and adenosine derivatives can be formulated into a liposome or microparticle, which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically uni-lamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGF-.beta., basic fibroblast growth factor (FGF2), epithelial growth factor (EGF), transforming growth factors alpha. and .beta. (TGF alpha. and beta.), nerve growth factor (NGF), platelet-derived growth factor (PDGF), and vascular endothelial growth factor/vascular permeability factor (VEGF/VPF), antiviral, antibacterial, anti-inflammatory, immuno-suppressant, analgesic, vascularizing agent, and cell adhesion molecule.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Although the first model is useful in patients undergoing coronary artery bypass surgery, and constitutes proof of principle that one local injection induces angiogenesis, a broader approach using a second model can also be used. In the second model, a catheter retrograde is placed into the left ventricle via a carotid artery in the anesthetized rat prior to inducing myocardial infarction. Alternatively, a direct needle puncture of the aorta, just above the aortic valve, is performed. The intracoronary injection of the Low Molecular Weight Sulfated saccharide is then simulated by abruptly occluding the aorta above the origin of the coronary vessels for several seconds, thereby producing isovolumic contractions. Low Molecular Weight Sulfated saccharide is then injected into the left ventricle or aorta immediately after aortic constriction. The resulting isovolumic contractions propel blood down the coronary vessels perfusing the entire myocardium with Low Molecular Weight Glycosamino glycans. This procedure can be done as many times as necessary to achieve effectiveness. The number of injections depends on the doses used and the formation of new blood vessels.

Compositions and methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of Low Molecular Weight Glycosamino glycans, polymeric forms, and derivatives. The methods involve the co-administration of an effective amount of Low Molecular Weight Glycosamino glycans, polymeric forms, and derivatives in low, daily dosages for a week or more.

This invention provides novel compositions and methods for treatment of occlusive peripheral vascular disease and coronary diseases, in particular, the occlusion of coronary vessels, and disorders associated with the occlusion of the peripheral vasculature and/or coronary blood vessels, are disclosed. Also disclosed are compositions and methods for promoting angiogenesis and/or recruiting collateral blood vessels in a patient in need thereof. The compositions include an effective amount of polymeric forms of Low Molecular Weight Glycosamino glycans, analogs and derivatives, with an effective amount of an adenosine and/or nitric oxide donor or other vasodilators. The compositions can be in the form of a sterile, injectable, pharmaceutical formulation that includes an angiogenically effective amount of Low Molecular Weight Glycosamino glycans, polymeric forms or their combinations and adenosine derivatives in a physiologically and pharmaceutically acceptable carrier, optionally with one or more excipients.

The methods involve the co-administration of an effective amount of Low Molecular Weight Glycosamino glycans, polymeric forms or their combinations and an effective amount of an apomorphine, adenosine and/or NO donor in low, daily dosages for a week or more. One or both components can be delivered locally via catheter. Low Molecular Weight Glycosamino glycans, polymeric forms or their combinations can be delivered to capillary beds surrounding ischemic tissue by incorporation of the compounds in an appropriately sized liposome or microparticle. Low Molecular Weight Glycosamino glycans, polymeric forms or their combinations can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart, for example, occlusive peripheral vascular disease (also known as peripheral arterial occlusive disease), where decreased blood flow is a problem.

While embodiments of the present invention have been described herein for purposes of illustration, many modifications and changes will become apparent to those skilled in the art. accordingly, the appended claims are intended to encompass all such modifications and changes as fall within the true spirit and scope of this invention.

What is claimed is:

1. A composition, comprising a branched sulfated saccharide conjugated to a polymer, said sulfated saccharide having a molecular weight less than 5000 Dalton, said composition configured to be administered to a subject for treating the subject with the sulfated saccharide with respect to a pathological condition comprised by the subject, wherein the sulfated saccharide is conjugated to the polymer by being non-covalently bonded to the polymer, and wherein the sulfated saccharide that is non-covalently bonded to the polymer is encapsulated within a nano-particle haying a linear dimension less than 200 nanometers.

2. A composition, comprising a branched sulfated saccharide conjugated to a polymer, said sulfated saccharide having a molecular weight less than 5000 Dalton, said composition configured to be administered to a subject for treating the subject with the sulfated saccharide with respect to a pathological condition comprised by the subject, wherein the composition further comprises a pro-angiogenesis factor, a vasodilator, an agent, and combinations thereof, and wherein the agent selected from the group consisting of a neuroprotective agent, a memory enhancer, a nerve cell regeneration agent, and combinations thereof.

3. The composition of claim 2 wherein the sulfated saccharide is conjugated to the polymer by being covalently bonded to the polymer.

4. The composition of claim 3, wherein the sulfated saccharide is covalently bonded to the polymer via an ester linkage.

5. The composition of claim 4, wherein the sulfated saccharide is covalently bonded to the polymer via said ester linkage using polyvinyl alcohol.

6. The composition of claim 3, wherein the sulfated saccharide is covalently bonded to the polymer via an anhydride linkage.

7. The composition of claim 6, wherein the sulfated saccharide is covalently bonded to the polymer via said anhydride linkage using acrylic acid ethylene co-polymer.

8. A composition, comprising a branched sulfated saccharide conjugated to a polymer, said sulfated saccharide having a molecular weight less than 5000 Dalton, said composition configured to be administered to a subject for treating the subject with the sulfated saccharide with respect to a pathological condition comprised by the subject, wherein the sulfated saccharide is conjugated to the polymer by being non-covalently bonded to the polymer, and wherein the sulfated saccharide is non-covalently bonded to the polymer by being entrapped in a polylactic acid (PLA) polymer.

9. The composition of claim 1, wherein the sulfated saccharide is a sulfated oligosaccharide.

10. The composition of claim 9, wherein the sulfated oligosaccharide is selected from the group consisting of a sulfated tetraoligosaccharide, a sulfated pentaoligosaccharide, a sulfated hexaoligosaccharide, a sulfated septaoligosaccharide, and a sulfated octaoligosaccharide.

11. The composition of claim 1, wherein the polymer is a linear polymer.

12. The composition of claim 1, wherein the polymer is a branched polymer.

13. The composition of claim 12, wherein the branched polymer comprises a dendrimer.

14. A composition, comprising a branched sulfated saccharide conjugated to a polymer, said sulfated saccharide having a molecular weight less than 5000 Dalton, said composition configured to be administered to a subject for treating the subject with the sulfated saccharide with respect to a pathological condition comprised by the subject, wherein the polymer is polyethylene glycol (PEG).

15. The composition of claim 1, wherein the polymer is biodegradable.

16. The composition of claim 1, wherein the polymer is non-biodegradable.

17. The composition of claim 2, wherein the composition comprises the pro-angiogenesis factor, and wherein the pro-angiogenesis factor is selected from the group consisting of fibroblast growth factor (FGF), vascular endothelial growth factor (VEGF), and a combination thereof.

18. The composition of claim 2, wherein the composition comprises the vasodilator, and wherein the vasodilator is selected from the group consisting of a nitric oxide donor, an adenosine analog, a phosphodiesterase inhibitor, apomorphine, and combinations thereof.

19. A method for forming the composition of claim 1, said method comprising non-covalently conjugating the sulfated saccharide to the polymer.

20. A method of treating an individual for an impairment of health, said method comprising administering the composition of claim 1 to the individual to treat the individual with respect to the impairment, wherein the individual is the subject, wherein the impairment is the pathological condition, and wherein the pathological condition is selected from the group consisting of occlusive vascular disease, coronary disease, erectile dysfunction, myocardial infarction, ischemia, stroke, peripheral artery vascular disorder, neuronal injury, a spinal cord injury, trauma, neuropathy, Alzheimer disease, a wound, erectile dysfunction, and combinations thereof.

21. A method of treating an individual for an impairment of health, said method comprising administering the composition of claim 2 to the individual to treat the individual with respect to the impairment, wherein the individual is the subject, wherein the impairment is the pathological condition, and wherein the pathological condition is selected from the group consisting of occlusive vascular disease, coronary disease, erectile dysfunction, myocardial infarction, ischemia, stroke, peripheral artery vascular disorder, neuronal injury, a spinal cord injury, trauma, neuropathy, Alzheimer disease, a wound, erectile dysfunction, and combinations thereof.

22. The method of claim 21, wherein the sulfated saccharide is conjugated to the polymer by being covalently bonded to the polymer.

23. The method of claim 22, wherein the sulfated saccharide is covalently bonded to the polymer via an ester linkage.

24. The method of claim 23, wherein the sulfated saccharide is covalently bonded to the polymer via said ester linkage using polyvinyl alcohol.

25. The method of claim 22, wherein the sulfated saccharide is covalently bonded to the polymer via an anhydride linkage.

26. The method of claim 25, wherein the sulfated saccharide is covalently bonded to the polymer via said anhydride linkage using acrylic acid ethylene co-polymer.

27. The method of claim 20, wherein the sulfated saccharide is non-covalently bonded to the polymer by being entrapped in a polylactic acid (PLA) polymer.

28. The method of claim 20, wherein the sulfated saccharide is a sulfated oligosaccharide.

29. The method of claim 28, wherein the sulfated oligosaccharide is selected from the group consisting of a sulfated tetraoligosaccharide, a sulfated pentaoligosaccharide, a sulfated hexaoligosaccharide, a sulfated septaoligosaccharide, and a sulfated octaoligosaccharide.

30. The method of claim 20, wherein the polymer is a linear polymer.

31. The method of claim 20, wherein the polymer is a branched polymer.

32. The method of claim 31, wherein the branched polymer comprises a dendrimer.

33. The method of claim 20, wherein the polymer is polyethylene glycol (PEG).

34. The method of claim 20, wherein the polymer is biodegradable.

35. The method of claim 20, wherein the polymer is non-biodegradable.

36. The method of claim 20, wherein the subject is a human being.

37. The method of claim 20, wherein the subject is selected from the group consisting of a monkey, a cow, a sheep, a horse, a pig, a goat, a dog, a cat, a mouse, a rat, a cultured cells, and transgenic species thereof.

38. The method of claim 20, wherein the pathological condition is selected from the group consisting of occlusive vascular disease, coronary disease, erectile dysfunction, myocardial infarction, ischemia, stroke, peripheral artery vascular disorder, neuronal injury, a spinal cord injury, trauma, neuropathy, Alzheimer disease, a wound, and combinations thereof.

39. The method of claim 20, wherein the pathological condition comprises the occlusive vascular disease, and wherein the occlusive vascular disease is selected from the group consisting of a venous thromboembolic disorder, an arterial thromboembolic disorder, and a combination thereof.

40. The method of claim 39, wherein the occlusive vascular disease comprises the venous thromboembolic disorder, and wherein the venous thromboembolic disorder is selected from the group consisting of a deep vein thrombosis, a sickle cell disease, a pulmonary embolism, and combinations thereof.

41. The method of claim 39, wherein the occlusive vascular disease comprises the arterial thromboembolic disorder, and wherein the arterial thromboembolic disorder is selected from the group consisting of a coronary artery disease, a cerebrovascular disorder, and a combination thereof.

42. The method of claim 20, wherein the pathological condition comprises erectile dysfunction.

43. The method of claim 42, wherein the composition further comprises a vasodilator.

44. The method of claim 43, wherein the vasodilator is selected from the group consisting of a nitric oxide donor, an adeno sine analog, a phosphodiesterase inhibitor, apomorphine, and combinations thereof.

45. The composition of claim 1, wherein the sulfated saccharide is selected from the group consisting of a sulfated tetrasaccharide, a sulfated hexasaccharide, a sulfated octasaccharide, and a sulfated decasaccharide.

46. The composition of claim 45, wherein the sulfated saccharide consists of the sulfated tetrasaccharide.

47. The composition of claim 45, wherein the sulfated saccharide consists of the sulfated hexasaccharide.

48. The composition of claim 45, wherein the sulfated saccharide consists of the sulfated octasaccharide.

49. The composition of claim 45, wherein the sulfated saccharide consists of the sulfated decasaccharide.

50. A method for forming the composition of claim 2, said method comprising conjugating the sulfated saccharide to the polymer.

51. The method of claim 21, wherein the subject is a human being.

52. The method of claim 21, wherein the subject is selected from the group consisting of a monkey, a cow, a sheep, a horse, a pig, a goat, a dog, a cat, a mouse, a rat, a cultured cells, and transgenic species thereof.

53. The method of claim 21, wherein the pathological condition is selected from the group consisting of occlusive vascular disease, coronary disease, erectile dysfunction, myocardial infarction, ischemia, stroke, peripheral artery vascular disorder, neuronal injury, a spinal cord injury, trauma, neuropathy, Alzheimer disease, a wound, and combinations thereof.

54. The method of claim 21, wherein the pathological condition comprises the occlusive vascular disease, and wherein the occlusive vascular disease is selected from the group consisting of a venous thromboembolic disorder, an arterial thromboembolic disorder, and a combination thereof.

55. The method of claim 54, wherein the occlusive vascular disease comprises the venous thromboembolic disorder, and wherein the venous thromboembolic disorder is selected from the group consisting of a deep vein thrombosis, a sickle cell disease, a pulmonary embolism, and combinations thereof.

56. The method of claim 54, wherein the occlusive vascular disease comprises the arterial thromboembolic disorder, and wherein the arterial thromboembolic disorder is selected from the group consisting of a coronary artery disease, a cerebrovascular disorder, and a combination thereof.

57. The method of claim 21, wherein the pathological condition comprises erectile dysfunction.

* * * * *

UNITED STATES PATENT AND TRADEMARK OFFICE
CERTIFICATE OF CORRECTION

PATENT NO.       : 7,741,311 B2
APPLICATION NO.  : 11/324702
DATED            : June 22, 2010
INVENTOR(S)      : Mousa et al.

It is certified that error appears in the above-identified patent and that said Letters Patent is hereby corrected as shown below:

Column 11

Line 22, delete "a" and insert -- α --

Line 24, after "with" insert -- 5 --

Hexa-β-D-glucopyranoside diagram, insert -- O -- at location indicated by arrow (arrow is depicted for illustrative purposes only):

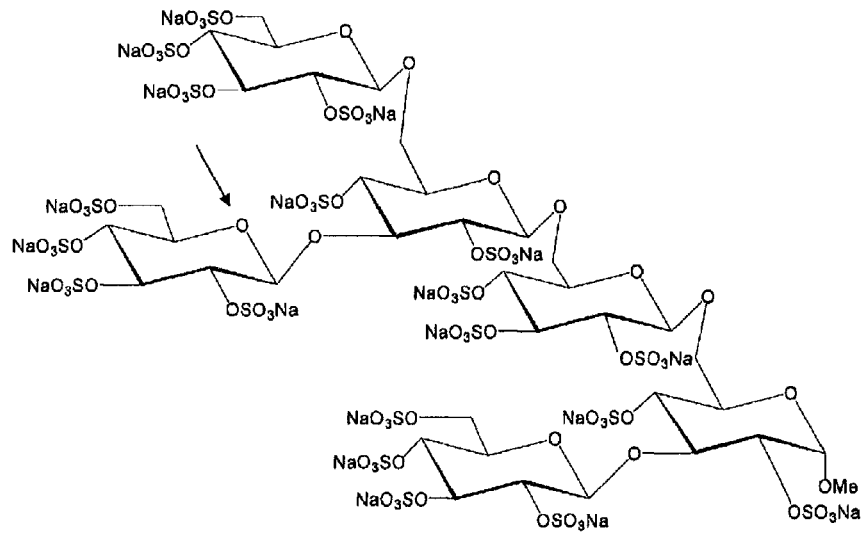

Column 12
Line 17, after "all three" delete "α" and insert -- β --

Signed and Sealed this

Fourteenth Day of September, 2010

David J. Kappos
*Director of the United States Patent and Trademark Office*

CERTIFICATE OF CORRECTION (continued)

U.S. Pat. No. 7,741,311 B2

Column 12 (continued)

Sulfated Octyl 3-O-methyl-Xylopyranosyl Hexasaccharide diagram, insert -- O -- at location indicated by arrow (arrow is depicted for illustrative purposes only):

Column 13

Line 50, after "pound 31" delete "/"

Column 15

Oligosaccharide diagram, insert -- n -- at location indicated by arrow (arrow is depicted for illustrative purposes only):

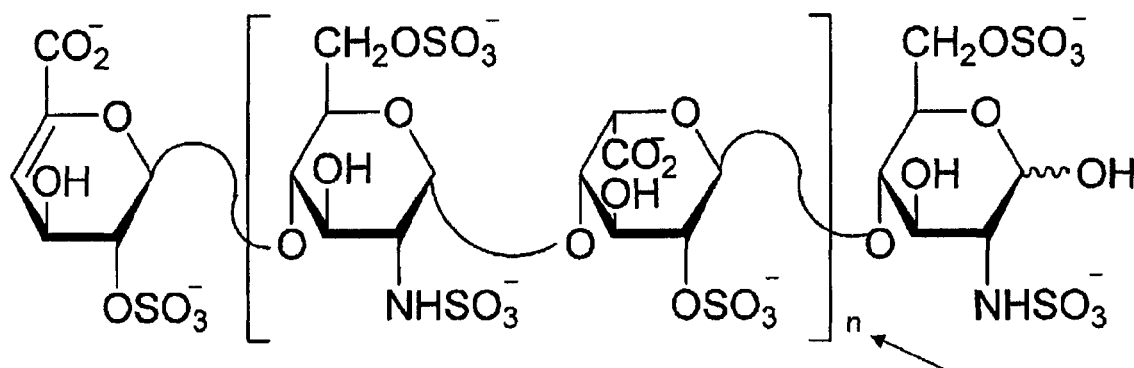

n = 0, DP 2, disaccharide
n = 1, DP 4, tetrasaccharide
n = 2, DP 6, hexasaccharide
n = 3, DP 8, octasaccharide
n = 4, DP 10, decasaccharide Line 64, after "EBM medium" delete "for"

Line 65, before "EC-beads" delete "add" and after "EC-beads" insert -- are added --

Column 20

Line 55, delete "removed"

Line 66, after "solution" insert -- and --

Column 29

Line 10, delete "parental" and insert -- parenteral --

Column 30

Line 43, delete "alpha." and insert -- .alpha. --

Column 31

Line 65, delete "accordingly" and insert -- Accordingly --

Column 34

Line 47, delete "adeno sine" and insert -- adenosine --